(12) United States Patent
Fishberger et al.

(10) Patent No.: US 10,538,377 B1
(45) Date of Patent: Jan. 21, 2020

(54) STETHOSCOPE COVER DISPENSING SYSTEM

(71) Applicants: Kenneth Irwin Fishberger, Setauket, NY (US); Ross Fishberger, Setauket, NY (US)

(72) Inventors: Kenneth Irwin Fishberger, Setauket, NY (US); Ross Fishberger, Setauket, NY (US)

( * ) Notice: Subject to any disclaimer, the term of this patent is extended or adjusted under 35 U.S.C. 154(b) by 0 days.

(21) Appl. No.: 16/412,830

(22) Filed: May 15, 2019

(51) Int. Cl.
  *B65D 83/08* (2006.01)
  *A61B 7/02* (2006.01)
(52) U.S. Cl.
  CPC ............ *B65D 83/0811* (2013.01); *A61B 7/02* (2013.01)
(58) Field of Classification Search
  CPC ..... E05B 1/0069; A61B 42/40; Y10T 16/458; A41D 13/081; B65H 16/005
  See application file for complete search history.

(56) References Cited

U.S. PATENT DOCUMENTS

| | | | | |
|---|---|---|---|---|
| 2,754,994 A * | 7/1956 | Cole | .................... | B65C 11/00 221/73 |
| 3,743,151 A * | 7/1973 | Malcolm | ............... | B65H 35/002 225/47 |
| 4,047,652 A * | 9/1977 | Ehrlund | .................... | G07B 3/02 225/54 |
| 4,111,333 A * | 9/1978 | Norgaard | ................. | A47J 47/01 221/73 |
| 4,669,678 A * | 6/1987 | Navarro | .............. | B65H 23/1955 242/413.6 |
| 4,824,517 A * | 4/1989 | Leahy | ..................... | B65C 11/00 156/759 |
| 5,065,896 A * | 11/1991 | Jurgich | ................. | B65C 9/0006 156/465 |
| 5,135,146 A * | 8/1992 | Simhaee | .............. | B65D 33/002 225/106 |
| 5,240,195 A * | 8/1993 | Klaassen | ............. | B65H 35/0026 206/411 |
| 5,261,563 A * | 11/1993 | Brimhall | ................. | B65C 11/00 221/71 |
| 5,553,809 A * | 9/1996 | Oku | ...................... | G03B 27/588 242/564.4 |
| 5,573,168 A * | 11/1996 | Kannankeril | .......... | B65H 35/10 225/106 |
| 5,863,384 A * | 1/1999 | Reddy | ..................... | B65C 11/00 156/576 |
| 5,938,070 A * | 8/1999 | Welborn | .............. | B65H 37/005 221/71 |

(Continued)

*Primary Examiner* — Gene O Crawford
*Assistant Examiner* — Ayodeji T Ojofeitimi
(74) *Attorney, Agent, or Firm* — Sorell, Lenna & Schmidt, LLP

(57) ABSTRACT

A dispenser includes side walls, a back wall and front walls. The housing includes an engaging wall. The walls define a cavity. The dispenser includes a wedge extending from the engaging wall, a first opening and a second opening. A roll is positioned within the cavity. A first end of a strip is wound about the roll. Covers are coupled to the strip. The covers each include first and second sides. The first sides directly engage the strip. A roller extends through the side walls. A portion of the strip extends through the first opening and over the wedge. A second end of the strip extends through the second opening and is wound about the roller. Systems, kits and methods of use are disclosed.

20 Claims, 20 Drawing Sheets

(56) References Cited

U.S. PATENT DOCUMENTS

| | | | | |
|---|---|---|---|---|
| 5,975,083 | A | * | 11/1999 | Henderson, Jr. ...... A41D 13/082 128/878 |
| 6,171,439 | B1 | * | 1/2001 | Groeneweg ............. B65C 11/00 156/714 |
| 6,206,134 | B1 | * | 3/2001 | Stark ........................ A61B 7/02 181/131 |
| 6,874,554 | B2 | * | 4/2005 | Chandaria .......... B65H 35/0033 156/527 |
| 7,117,971 | B1 | * | 10/2006 | Cornacchia .............. A61B 7/02 181/131 |
| 8,177,156 | B1 | * | 5/2012 | Rinne .................... A47K 10/34 242/564.4 |
| 8,196,774 | B1 | * | 6/2012 | Clarke .................. A61J 7/0409 221/13 |
| 8,757,435 | B2 | * | 6/2014 | Van Oort ........... B65D 83/0472 221/197 |
| 9,986,965 | B2 | * | 6/2018 | Fishberger ............... A61B 7/02 |
| 2007/0062998 | A1 | * | 3/2007 | Kanbar .................... B26F 3/02 225/56 |
| 2012/0138625 | A1 | * | 6/2012 | Case ..................... A47K 10/42 221/30 |
| 2013/0175289 | A1 | * | 7/2013 | Sternberg ............. B65C 9/1869 221/70 |
| 2016/0135652 | A1 | * | 5/2016 | Cittadino ............... A47K 10/38 312/34.8 |
| 2017/0258435 | A1 | * | 9/2017 | Fishberger ............... A61B 7/02 |
| 2019/0104896 | A1 | * | 4/2019 | Huang ................. B65H 16/005 |

* cited by examiner

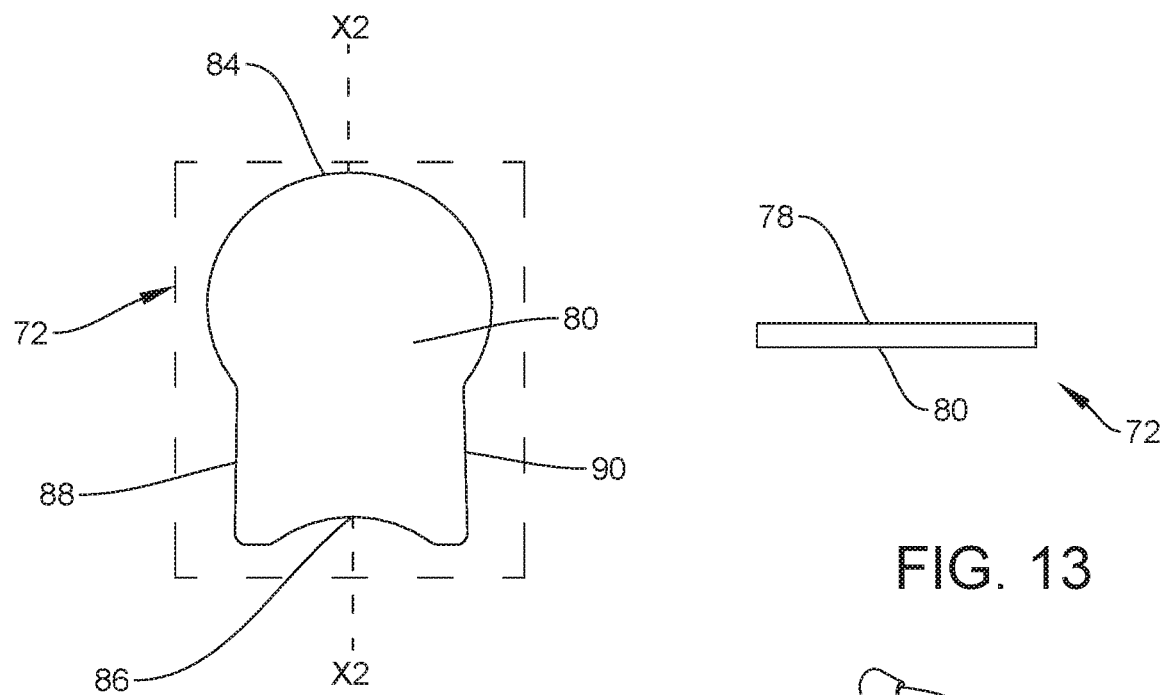
FIG. 12
FIG. 13
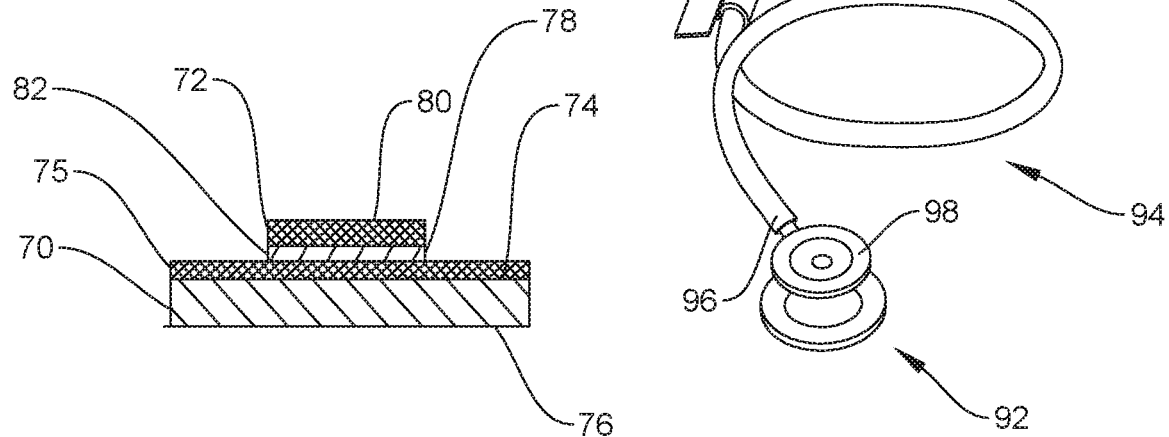
FIG. 14
FIG. 15

STETHOSCOPE COVER DISPENSING SYSTEM

TECHNICAL FIELD

The present disclosure generally relates to medical devices, and more particularly to instrument covers and a dispensing system that stores and dispenses the instrument covers for application with various medical devices such as, for example, stethoscopes. Methods of use and kits are also disclosed.

BACKGROUND

A stethoscope is an acoustic medical device typically used by a physician or medical care provider to monitor sounds in a patient's organs and/or pathways (respiratory, cardiac, arterial, etc.). Stethoscopes typically include a chest piece for placement against the patient for sensing relatively high frequency sound, an air-filled hollow tube to transmit the sound from the chest piece, and ear tubes to receive the sound from the air-filled hollow tube and transmit the sound via ear tips to the physician or medical care provider. The chest piece is generally known to include a head and a diaphragm, which is the part of the chest piece placed against the patient. When the diaphragm is placed on the patient, bodily sounds vibrate the diaphragm creating acoustic pressure sound waves which travel up the air-filled hollow tube and ear tubes to the physician or medical care provider's ears. The physician or medical care provider may then be better able to diagnose a condition or whether the patient's organs or pathways are functioning normally.

In use, the head and diaphragm of a stethoscope can easily be contaminated with bacteria and other contaminants as stethoscopes are typically used on several different patients every hour, the patients being affected by different contaminants. Physicians or medical care providers in a hospital setting see about 20-30 patients an hour including neonatal and pediatric patients, surgery patients, cancer and infectious disease patients and often examine these patients using the same stethoscope. Medical providers typically employ a stethoscope on most of the patients they see in a hospital setting and anywhere between 6-12 patients per hour in an office setting. Transmission of bacterial infections among patients, particularly in a hospital setting, is of great concern especially in view of the development of antibiotic-resistant strains of staphylococcal infections and other resistant strains of bacteria, viruses, and fungal infections. Examples of resistant strains of bacteria include but are limited to, vancomycin resistant *enterococcus* and *clostridium dificile*; viruses such as hepatitis B and C; and fungal infections such as aspergillosis *candida*.

Conventional stethoscope covers include a thin sheet of plastic having an adhesive backing which can be applied over the diaphragm of a stethoscope before use on each new patient. After use, the cover is typically removed and discarded. These covers can function adequately; however, problems arise with the use of such covers. Such problems include the cover falling off the stethoscope during application, the cover not fitting with an air-tight seal on the diaphragm during application, poor acoustic transmission and the transmission of microorganisms, fluids or other contaminants to the head of the stethoscope and in some cases, the diaphragm of the stethoscope. Additionally, dispensers for such covers are often cumbersome and/or make it difficult to dispense the covers. This disclosure describes an improvement over these prior art technologies.

SUMMARY

In one embodiment, in accordance with the present disclosure, a dispenser is provided that includes a housing comprising opposite first and second side walls. The housing comprises a back wall and spaced apart first and second front walls. The back wall and the front walls each extend from the first side wall to the second side wall. The housing comprises an engaging wall extending from the first front wall to the second front wall. Inner surfaces of the walls define a cavity. The housing comprises a wedge extending from the engaging wall. A space between the wedge and the engaging wall defines a first opening. A space between the engaging wall and the front wall defines a second opening. The openings are in communication with the cavity. A roll is positioned within the cavity. A first end of a strip is wound about the roll. A plurality of spaced apart covers are coupled to the strip. The covers each comprise a first side and an opposite second side. The first sides directly engage the strip. A roller extends through the side walls. An intermediate portion of the strip extends through the first opening and over an outer surface of the wedge. A second end of the strip extends through the second opening such that a portion of the second end is wound about the roller.

In some embodiments, the covers are instrument covers configured to cover a portion of an instrument, such as, for example, a diaphragm of a stethoscope. In some embodiments, the instrument covers are separated from one another by a series of perforations. In some embodiments, the instrument covers are spaced apart from one another on the strip. In some embodiments, the instrument covers are acoustically transmissive and substantially impermeable to microorganisms and fluids. In some embodiments, the instrument covers each comprise a first surface and an opposite second surface having non-stick properties that prevent the second surface from permanently adhering to a strip. In some embodiments, the second surface prevents the instrument covers from permanently adhering to the strip such that the instrument covers can be easily removed from the strip. In some embodiments, static cling from the second surface and/or the strip removably couples the instrument covers to the strip. In some embodiments, the first surface comprises a material having adhesion properties. In some embodiments, the first surface is configured to be removably attached to the head of a stethoscope such that the instrument cover will not fall off the stethoscope during use by a physician or medical provider. In some embodiments, the first surface is made of a material having adhesion properties. In some embodiments, the first surface is coated with a material having adhesion properties. In some embodiments, the strip is provided in a roll such that the second surfaces of the instrument covers contact one another to maintain the strip and the instrument covers in a roll.

In some embodiments, each of the instrument covers is sized and configured to removably cover the diaphragm and the head of a stethoscope simultaneously by form-fitting a respective first surface with outer surfaces of the diaphragm and the head. In some embodiments, the instrument covers are made from one or more of polyvinyl chloride, polyvinylidene chloride, low density polyethylene, linear low density polyethylene, polyisobutene, poly[ethylene-vinylacetate] copolymer and lightweight aluminum foil. In some embodiments, the instrument covers are made from one or more of a cellophane, vinyl, acetate, polyethylene acrylic, butyl rubber, ethylene-vinyl acetate, natural rubber, a nitrile, silicone rubber, a styrene block copolymer, a vinyl ether and a tackifier. In some embodiments, the instrument covers each include an antimicrobial substance that can neutralize or destroy microbes. In some embodiments, the material(s) that form(s) the instrument covers comprises the antimicrobial substance. That is, the antimicrobial substance is distributed throughout a thickness of each of the instrument covers and/or on the first and/or second surfaces of the instrument covers. In some embodiments, at least one of the first and second surfaces is coated with the antimicrobial substance.

In some embodiments, the housing comprises an antimicrobial material. In some embodiments, the housing is configured for mounting on a vertical surface, such as, for example, a wall or a horizontal surface, such as, for example, a table. In some embodiments, an antimicrobial ultraviolet light source is positioned within the cavity of the housing. In some embodiments, the housing is disposable and may be made from materials, such as, for example, cardboard. In some embodiments, the housing is reusable and may be made from materials, such as, for example, plastic.

In one embodiment, in accordance with the principles of the present disclosure, a method for dispensing instrument covers is provided. The method comprises rotating the roller relative to the housing to move the covers from a first orientation in which the second side of a respective one of the covers faces and is spaced apart from an outer surface of the engaging wall to a second orientation in which the second side of the respective one of the covers is spaced apart from the strip and directly engages the outer surface of the engaging wall. In some embodiments, the method further comprises contacting the respective one of the covers that is spaced apart from the strip with a portion of a stethoscope, such as, for example, a head of a stethoscope, and positioning the instrument cover that is spaced apart from the strip about the head. In some embodiments, positioning the instrument cover comprises crimping the instrument cover about the head and/or at least a portion of a hollow tube of the stethoscope that is coupled to the head of the stethoscope. In some embodiments, the method includes rotating the roller relative to the housing to move the strip such that the second side of a respective second one of the covers is spaced apart from the strip and directly engages the outer surface of the engaging wall.

In one embodiment, in accordance with the principles of the present disclosure, a kit is provided. The kit comprises the dispenser and at least one stethoscope. In some embodiments, the kit further comprises at least one box of gloves.

In one embodiment, in accordance with the principles of the present disclosure, a dispenser includes a housing comprising opposite first and second side walls. The housing comprises a back wall and spaced apart first and second front walls. The back wall and the front walls each extend from the first side wall to the second side wall. The housing comprises an engaging wall extending from the first front wall to the second front wall. Inner surfaces of the walls define a cavity. The housing comprises a wedge extending from the engaging wall. A space between the wedge and the engaging wall defines a first opening. A space between the engaging wall and the front wall defines a second opening. The openings are in communication with the cavity. A roll is positioned within the cavity. A first end of a strip is wound about the roll. A plurality of spaced apart covers are coupled to the strip. The strip comprises a backing paper including a first side and a second side. The first side of the backing paper is coated with a polyolefin. The covers are made from a polyimide. The covers each comprise a first side and an opposite second side. An acrylates copolymer is positioned between the first sides of the covers and the polyolefin coating to couple the covers to the strip. A roller extends through the side walls. An intermediate portion of the strip extends through the first opening and over an outer surface of the wedge. A second end of the strip extends through the second opening such that a portion of the second end is wound about the roller. The roller is rotatable relative to the housing to move the covers from a first orientation in which the second side of a respective one of the covers faces and is spaced apart from an outer surface of the engaging wall to a second orientation in which the second side of the respective one of the covers is spaced apart from the strip and directly engages the outer surface of the engaging wall.

In one embodiment, in accordance with the principles of the present disclosure, a dispenser includes a housing comprising opposite first and second side walls. The housing comprises a back wall and spaced apart first and second front walls. The back wall and the front walls each extend from the first side wall to the second side wall. The housing comprises an engaging wall extending from the first front wall to the second front wall. Inner surfaces of the walls define a cavity. The housing comprises a wedge extending from the engaging wall. A space between the wedge and the engaging wall defines a first opening. A space between the engaging wall and the front wall defines a second opening. The openings are in communication with the cavity. A roll is positioned within the cavity. A first end of a strip is wound about the roll. A plurality of spaced apart covers are coupled to the strip. The strip comprises a backing paper including a first side and a second side. The first side of the backing paper is coated with a polyolefin. The covers are made from a polyimide. The covers each comprising a first side and an opposite second side. An acrylates copolymer being positioned between the first sides of the covers and the polyolefin coating to couple the covers to the strip. A roller extends through the side walls. An intermediate portion of the strip extends through the first opening and over an outer surface of the wedge. A second end of the strip extends through the second opening such that a portion of the second end is wound about the roller. An actuator is configured to rotate the roller relative to the housing. A sensor is in communication with the actuator. The sensor is configured to send a signal to the actuator in response to an audio command or a visual command detected by the sensor. The actuator is configured to rotate the roller relative to the housing upon receiving the signal from the sensor. The roller is rotatable relative to the housing to move the covers from a first orientation in which the second side of a respective one of the covers faces and is spaced apart from an outer surface of the engaging wall to a second orientation in which the second side of the respective one of the covers is spaced apart from the strip and directly engages the outer surface of the engaging wall.

BRIEF DESCRIPTION OF THE DRAWINGS

The present disclosure will become more readily apparent from the specific description accompanied by the following drawings, in which:

FIG. 12 is a top view of one embodiment of a component of the dispensing system shown in FIG. 1, in accordance with the principles of the present disclosure;

FIG. 13 is side view of one embodiment of a component of the dispensing system shown in FIG. 1, in accordance with the principles of the present disclosure;

FIG. 14 is a side, cross-sectional view of one embodiment of components of the dispensing system shown in FIG. 1, in accordance with the principles of the present disclosure;

FIG. 15 is a perspective view of a component of the dispensing system shown in FIG. 1;

Like reference numerals indicate similar parts throughout the figures.

DETAILED DESCRIPTION

Figure 1:
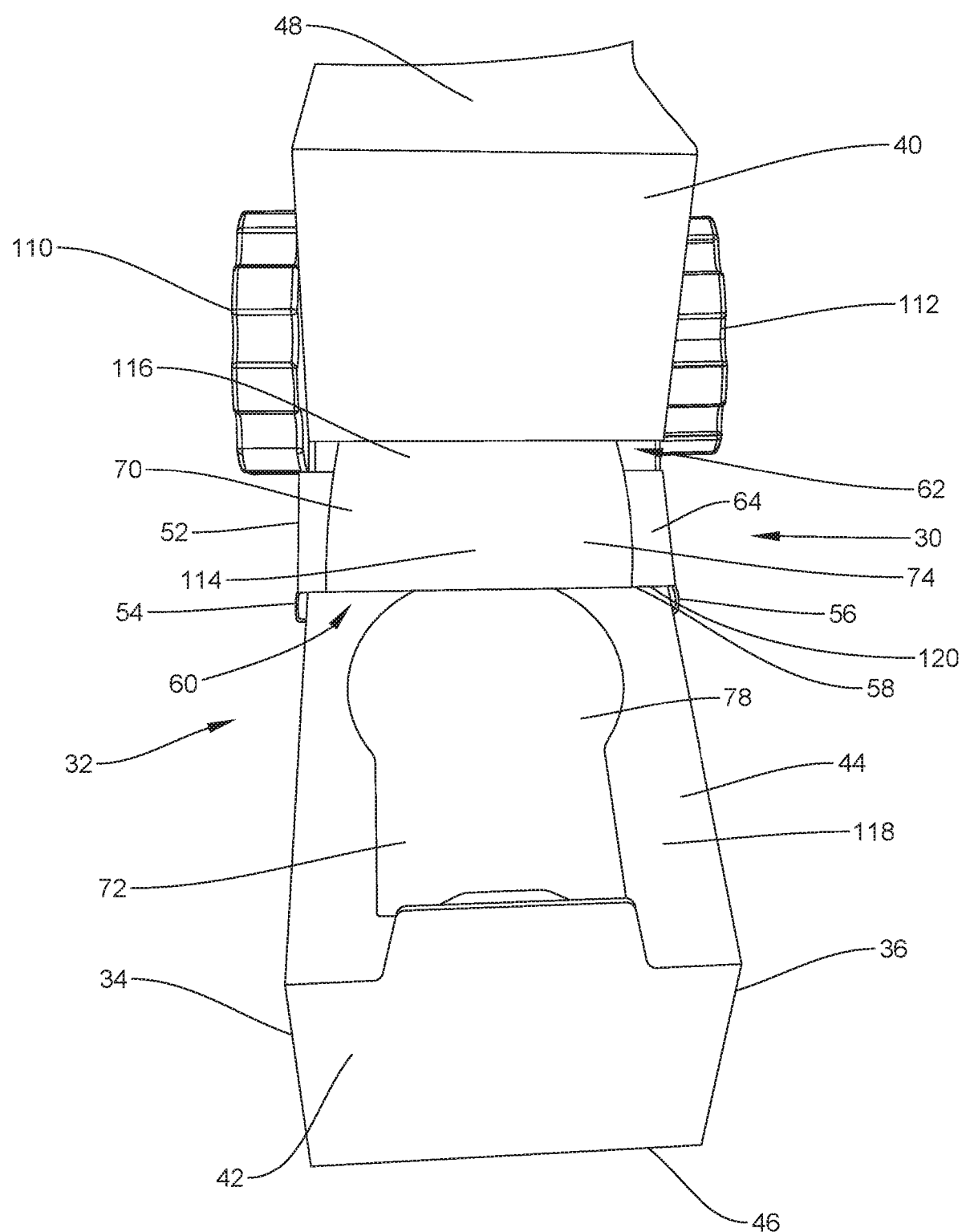
FIG. 1 is a perspective, front view of one embodiment of a dispensing system in accordance with the principles of the present disclosure.
Figure 2:
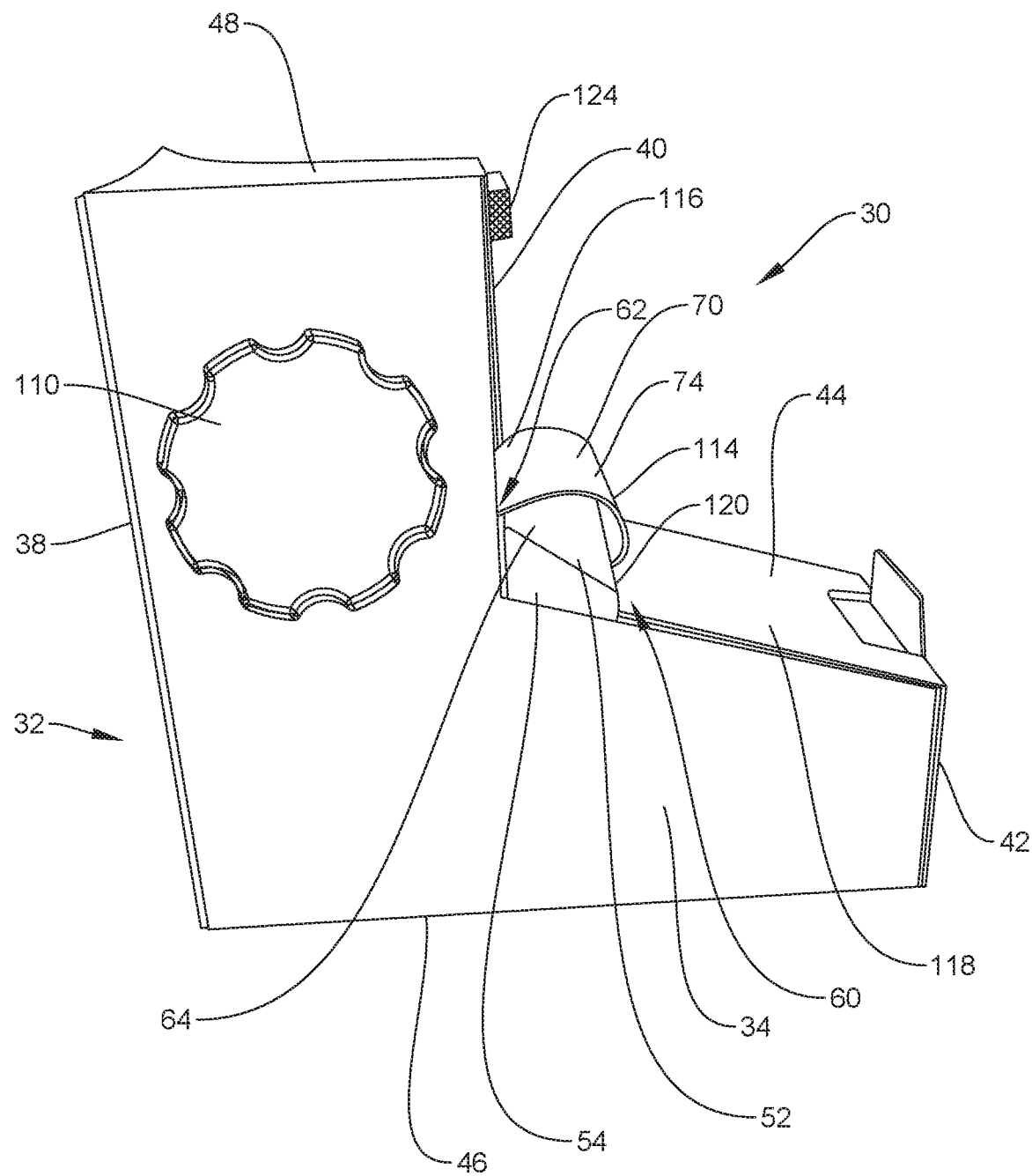
FIG. 2 is a perspective, side view of the dispensing system shown in FIG. 1.
Figure 3:
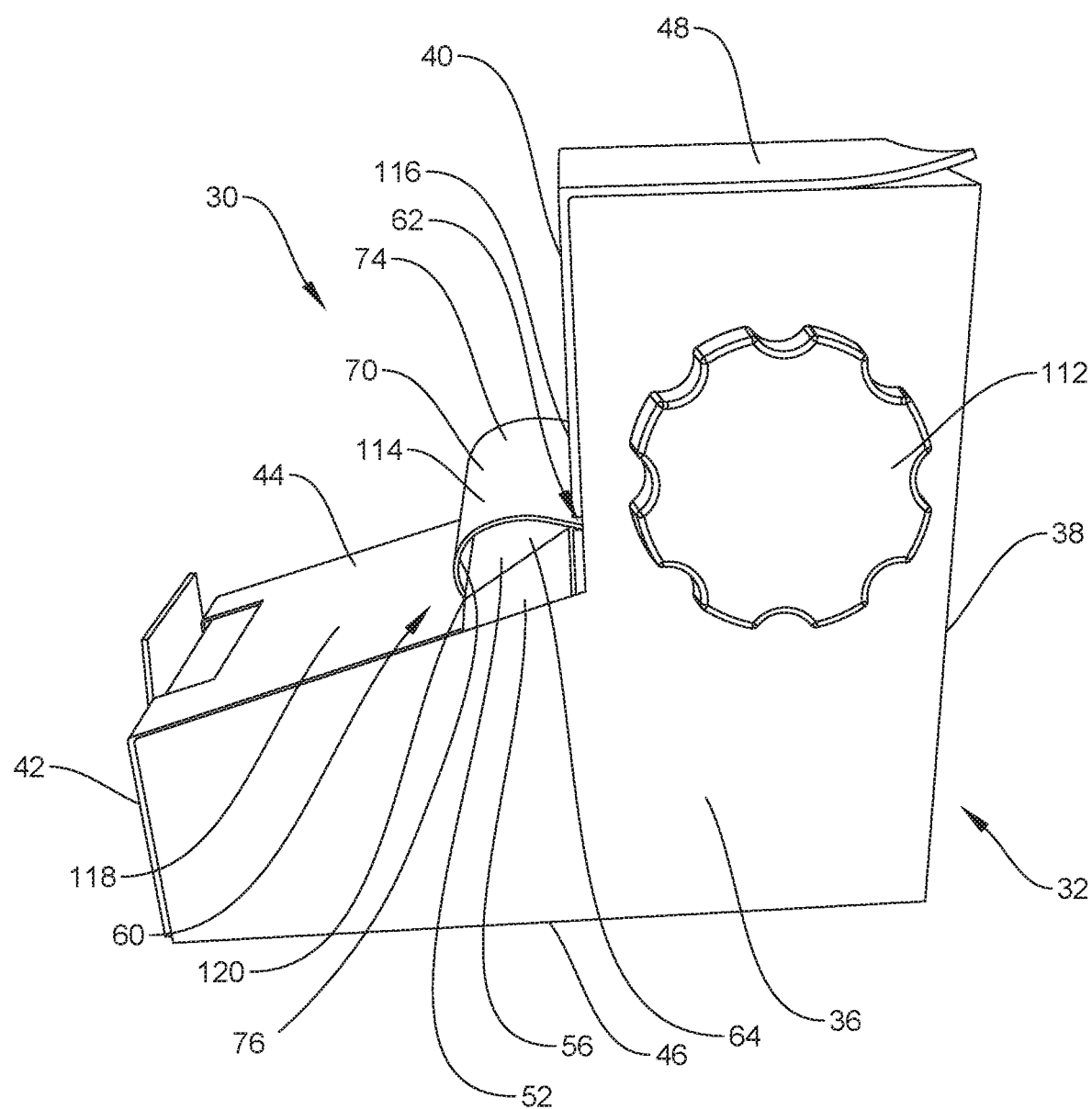
FIG. 3 is a perspective, side view of the dispensing system shown in FIG. 1.
Figure 4:
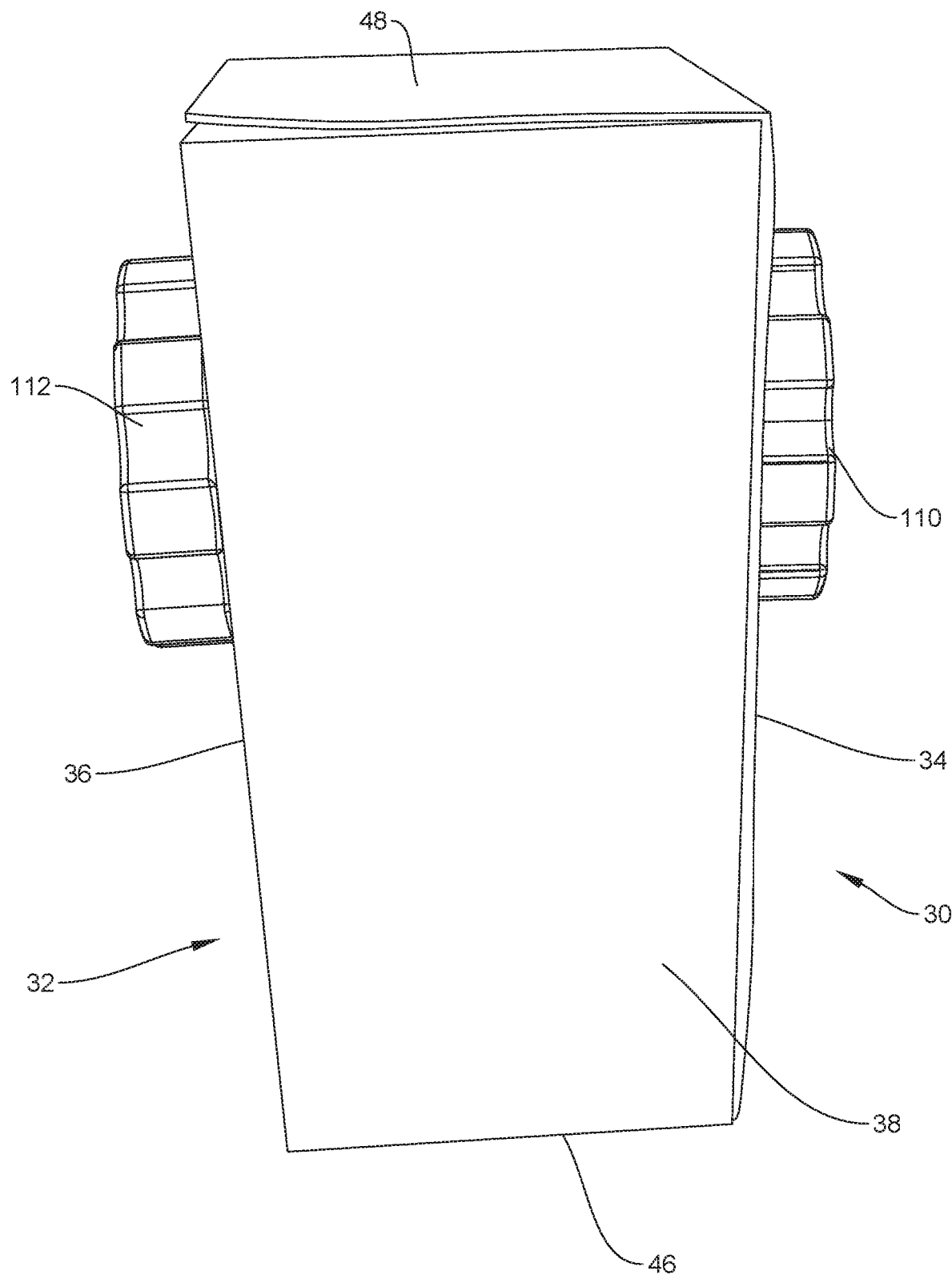
FIG. 4 is a perspective, rear view of the dispensing system shown in FIG. 1.

The exemplary embodiments of the dispensing system and related methods of use disclosed are discussed in terms of medical devices, and more particularly to a dispensing system that stores and dispenses covers for medical devices. It is envisioned that the dispensing system may be employed in a hospital setting or a medical practitioner's examination room or office. The dispensing system includes a housing configured to hold and dispense acoustically transmissive instrument covers. In some embodiments, the instrument covers are each configured to securely fit onto the head and/or diaphragm of a medical instrument, such as, for example, a stethoscope such that the instrument cover forms an air-tight seal without any air bubbles or wrinkling of the instrument cover to prevent cross-contamination from patient to patient.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

The following disclosure includes a description of a dispensing system for holding and dispensing instrument covers. The disclosure also includes a description of related methods of employing the disclosed dispensing system and a description of a kit that includes the disclosed dispensing system. Alternate embodiments are also disclosed. Reference will now be made in detail to the exemplary embodiments of the present disclosure, which are illustrated in the accompanying figures. Turning now to FIGS. 1-22, there are illustrated components of a dispensing system, such as, for example, a dispensing system 30 and embodiments in accordance with the principles of the present disclosure.

The components of system 30 can be fabricated from biologically acceptable materials suitable for medical applications, depending on the particular application and/or preference of a medical practitioner. For example, the components of system 30, individually or collectively, can be fabricated from materials such as cellophane, vinyl, acetate, polyethylene acrylic, butyl rubber, ethylene-vinyl acetate, natural rubber, a nitrile, silicone rubber, a styrene block copolymer, a vinyl ether, a tackifier, antimicrobial and/or antiseptic materials including but are not limited to: alcohols such as ethanol, 1-propanol and 2-propanol/isopropanol or mixtures of these alcohols; sodium bicarbonate; hydrogen peroxide; benzalkonium chloride; chlorhexidine; hexachlorophene; iodine compounds; and combinations thereof. Antimicrobial materials that can be used include but are not limited to: beta-lactam antibiotics (such as penicillin, cephalosporin); protein synthesis inhibitors (such as aminoglycosides, macrolides, tetracycline, chloramphenicol, polypeptides); sulphonamides; cotrimoxazole; quinolones; anti-viral agents; anti-fungal agents; anti-cancer drugs; anti-malarial drugs; anti-tuberculosis drugs; anti-leprotic drugs;

anti-protozoal drugs and combinations thereof. In some embodiments, the components of system 30, individually or collectively, can be fabricated from materials such as polyvinyl chloride, polyvinylidene chloride, low density polyethylene, linear low density polyethylene, polyisobutene, poly[ethylene-vinylacetate] copolymer, lightweight aluminum foil and combinations thereof. In some embodiments, the components of system 30, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 30 may have material composites, including the above materials, to achieve various desired characteristics such as strength, rigidity, elasticity, compliance, biomechanical performance, durability and radiolucency or imaging preference. It is envisioned that the components of system 30 may be comprise antimicrobial and/or antiseptic materials. The components of system 30, individually or collectively, may also be fabricated from a heterogeneous material such as a combination of two or more of the above-described materials. The components of system 30 may be monolithically formed or integrally connected.

System 30 includes a housing 32 comprising a side wall 34 and a side wall 36 opposite wall 34. Wall 36 extends parallel to wall 34. Housing 32 comprises a back wall 38, a front wall 42 that is spaced apart from wall 38 and a front wall 40 positioned between wall 38 and wall 42. Housing 32 extends along a longitudinal axis X1 between wall 38 and wall 42. In some embodiments, walls 38, 40, 42 extends parallel to one another. In some embodiments, walls 34, 36 each extend perpendicular to axis X1. In some embodiments, walls 38, 40, 42 each extend perpendicular to walls 34, 36. Walls 38, 40, 42 each extend from wall 34 to wall 36. Housing 32 comprises an engaging wall 44 extending from wall 40 to wall 42. Housing 32 comprises a bottom wall 46 extending from wall 34 to wall 36 and from wall 38 to wall 42. Housing 32 comprises a top wall 48 opposite wall 46. Wall 48 extends from wall 34 to wall 36 and from wall 38 to wall 40. Walls 46, 48 each extend parallel to axis X1. In some embodiments, wall 44 extends at an acute angle relative to axis X1 to position stethoscope covers for engagement with a portion of a stethoscope, as discussed herein.

An inner surface 34a of wall 34, an inner surface 36a of wall 36, an inner surface 38a of wall 38, an inner surface 40a of wall 40, an inner surface 42a of wall 42, an inner surface 44a of wall 44, an inner surface 46a of wall 46 and an inner surface 48a of wall 48 define a cavity 50. Housing 32 comprises a wedge 52 extending from wall 44. Housing 32 comprises spaced apart extensions 54, 56 that each extend from wall 44 to a bottom surface 58 of wedge 52 to connect wedge 52 with housing 32. A space between wedge 52 and wall 44 defines a first opening 60. A space between wall 44 and wall 40 defines a second opening 62. Opening 60 is spaced apart from opening 62 by wedge 52. Openings 60, 62 are in communication with cavity 50. Wedge 52 includes a top surface 64 opposite surface 58. In some embodiments, surface 58 extends parallel to axis X1 and surface 64 extends at an acute angle relative axis X1 and surface 58. In some embodiments, surface 58 and/or surface 64 may be disposed at alternate orientations, relative to axis X1, such as, for example, parallel, transverse, perpendicular and/or other angular orientations such as acute or obtuse, co-axial and/or may be offset or staggered.

In some embodiments, at least one of walls 34, 36, 48, 40, 42, 44, 46, 48 and/or wedge 52 comprises an antimicrobial material, such as, for example, a silver-based antimicrobial material, a copper-based antimicrobial material, chlorhexidene gluconate, benzalkonium chloride, a monoquaternary and/or polyquaternary ammonium salt-based antimicrobial material, a biguanide-based antimicrobial such as polyhexamethylene biguanide, triclosan, zinc pyrithione, an isothiazolinone-based antimicrobial, a 10,10'-oxybisphenoxarsine-based antimicrobial, a peptide-based antimicrobial, a natural antimicrobial such as hops extract, honey, a chitosan-based antimicrobial, and combinations thereof. In some embodiments, housing 32 is configured for mounting on a vertical surface such as, for example, a wall of a room, or a horizontal surface, such as, for example, a top surface of a desk or bench. In some embodiments, system 30 includes a bracket that is positioned on the vertical surface and/or the horizontal surface. In some embodiments, housing 32 is coupled the bracket and the bracket is positioned on the vertical surface and/or horizontal surface. In some embodiments, the bracket is mounted to the vertical surface and/or horizontal surface to fix the bracket to the vertical surface and/or horizontal surface. In some embodiments, housing 32 is disposable and comprises a material, such as, for example, cardboard. In some embodiments, housing 32 is reusable and comprises a material, such as, for example, plastic and/or metal.

A tubular roll 66 is positioned within cavity 50. A first end 68 of a strip 70 is wound about roll 66. A plurality of spaced apart covers 72 are coupled to strip 70. In some embodiments, roll 66 is unsupported within cavity 50 such strip 70 and/or covers 72 directly engage surface 38a and/or surface 46a. In some embodiments, strip 70 comprises a backing paper including a first side 74 and an opposite second side 76. Side 74 is coated with a polymer 75, such as, for example, a polyolefin, as best shown in FIG. 14. In some embodiments, covers 72 are made from a polymer, such as, for example, a polyimide. Covers 72 each comprise a first side 78 and an opposite second side 80. A copolymer 82, such as, for example, an acrylates copolymer is positioned between sides 78 of covers 72 and polymer 75 to couple covers 72 to strip 70, as best shown in FIG. 14. In some embodiments, side 76 is uncoated. In some embodiments, polymer 75 is selected from the group consisting of polyethylene, polypropylene, and combinations thereof. In some embodiments, polymer 75 is a thermoplastic polyolefin. In some embodiments, polymer 75 is an elastomeric polyolefin. In some embodiments, polymer 75 has a viscosity from 7,000 to less than 500,000 mPa-sec at 190° Celsius. In some embodiments, polymer 75 is a polyimide film. In some embodiments, covers 72 each consist of the polyimide. In some embodiments, the polyimide that covers 72 are made from is a thermoset polyimide. In some embodiments, the polyimide that covers 72 are made from is selected from the group consisting of Apical, Kapton, UPILEX, VTEC PI, Norton TH, Kaptrex and combinations thereof. In some embodiments, strip 70 and/or covers 72 are free of any glue or other adhesives and covers 72 are coupled directly to strip 70 by static electricity. In such embodiments, sides 78 of covers 72 directly engage side 74 of strip 70.

In some embodiments, covers 72 are each made from a single planar layer of material, such as, for example one of the materials discussed, above, the single layer of material being defined by the distance from side 78 to side 80. In some embodiments, covers 72 made from the single planar layer of material are not coated. In some embodiments, strip 70 and/or covers 72 are free of paper, paper fiber, wood pulp, bamboo, rice and/or cotton. In some embodiments, strip 70 and/or covers 72 comprises a non-absorbent material. In some embodiments, strip 70 and/or covers 72 are free of any absorbent materials. In some embodiments, strip 70 and/or covers 72 comprises a waterproof and/or water-resistant material. In some embodiments, strip 70 and/or covers 72 comprises a non-porous material. In some embodiments, strip 70 and/or covers 72 comprises a porous material wherein pores of the porous material are uniformly distributed. In some embodiments, the uniformly distributed pores have the same size or diameter. In some embodiments, the uniformly distributed pores are less than 0.5 microns. In some embodiments, the uniformly distributed pores are between 0.5 microns and 10 microns. In some embodiments, the uniformly distributed pores are greater than 10 microns. In some embodiments, covers 72 are transparent or translucent to allow a portion of an instrument, such as, for example, a head of a stethoscope to be viewed through covers 72 to facilitate coupling of covers 72 to the head of the stethoscope. For example, it is envisioned that covers 72 may be applied to the head of the stethoscope by hand by positioning one of covers 72 adjacent to the head of the stethoscope. Because covers 72 are transparent or translucent, the head of the stethoscope can be viewed through cover 72 and cover 72 can be moved relative to the head of the stethoscope to center cover 72 about the head of the stethoscope, for example. In some embodiments, covers 72 are a solid color and are free of any indicia to ensure that sound can pass through covers 72 without being altered.

In some embodiments, covers 72 are configured to be applied to a portion of a stethoscope 94, such as, for example, a head 92 of stethoscope 94 to prevent cross-contamination between stethoscope 94 and a patient, while still allowing stethoscope 94 to function properly. That is, covers 72 do not inhibit and/or reduce the ability of a physician or medical provider to listen to internal sounds of an animal or human body using stethoscope 94. In some embodiments, covers 72 are disposable. That is, covers 72 are each configured for one-time use with a single patient such that a physician or medical provider covers at least a portion of stethoscope 94 with a first cover 72. After examination is complete, the first cover 72 may be removed from stethoscope 94 and discarded. The physician or medical provider may cover at least a portion of the same stethoscope 94 with a second cover 72 before examining a second patient. This configuration reduces and/or prevents contamination from the first patient to the second patient.

In some embodiments, covers 72 each extend along a longitudinal axis X2 between a first end 84 and an opposite second end 86, as shown in FIG. 12. Covers 72 each include opposite sidewalls 88, 90 that each extend parallel to axis X2. End 84 bows outwardly from sidewalls 88, 90 and is convexly curved from sidewall 88 to sidewall 90. In some embodiments, end 84 has a uniform radius of curvature from sidewall 88 to sidewall 90. End 84 has a size and shape configured to cover head 92 of stethoscope 94 while end 86 is wrapped about at least a portion of tubing 96 of stethoscope 94. In some embodiments, strip 70 and/or covers 72 are the same or similar to the strips and covers disclosed in U.S. Pat. No. 9,986,965, which is expressly incorporated herein by reference, in its entirety.

In some embodiments, covers 72 each comprise a material that is acoustically transmissive and substantially impermeable to microorganisms and fluids. In some embodiments, covers 72 each comprise polyvinyl chloride, polyvinylidene chloride, low density polyethylene, linear low density polyethylene, polyisobutene, poly[ethylene-vinylacetate copolymer, lightweight aluminum foil and combinations thereof. In some embodiments, covers 72 each comprise a crimpable material configured to form-fit around at least head 92 of stethoscope 94. In some embodiments, the thickness of each cover 72 is in the range of from about 0.01 mm to about 0.8 mm. In some embodiments, covers 72 each have a thickness in the range of from about 0.1 mm to about 0.4 mm. In some embodiments, dispensing system 30 includes one or a plurality of stethoscopes, such as, for example, stethoscopes 94.

In some embodiments, sides 78 of covers 72 are sprayed or coated with a material having non-stick properties and/or is glossy to prevent the material having adhesion and/or adherent properties and/or the sides 78 of covers 72 from sticking to side 74 of strip 70. In some embodiments, the material having non-stick properties forms sides 78 of covers 72. That is, the material having non-stick properties is integrally formed with sides 78 of covers 72 to provide sides 78 with non-stick properties. In some embodiments, sides 78 of instrument 72 are coated with a powder to prevent the sides 78 from permanently sticking to side 74 of strip 70. In some embodiments, sides 78 of covers 72 are sprayed or coated with an agent comprising wax to prevent sides 78 of covers 72 from permanently sticking to side 74 of strip 70. In some embodiments, at least one of sides 78, 80 of covers 72 comprises an antimicrobial substance that can neutralize or destroy microbes. In some embodiments, at least side 74 of strip 70 and/or at least sides 78 of instrument covers 72 are made of a material that allows static electricity to form that causes covers 72 to stick to side 74 of strip 70.

In some embodiments, sides 78 of covers 72 are free of any adhesive material and side 74 of strip 70 includes an adhesive that is sprayed or coated on side 74 to allow covers 72 to adhere to side 74. In some embodiments, the adhesive is applied to strip 70 in a manner such that the adhesive forms a central stripe of adhesive material that extends the entire length of strip. In some embodiments, the sides 78 of covers 72 are made of a material that allows static electricity to form that causes covers 72 to stick to side 74 of strip 70 and side 74 of strip 70 includes adhesive that is sprayed or coated on side 74, thus providing a dual means to removably adhere covers 72 to strip 70. In some embodiments, side 74 of strip 70 are free of any adhesive material.

In some embodiments, sides 78 of covers 72 are each made from and/or coated with a material having adhesion and/or adherent properties to allow covers 72 to removably adhere to at least a portion of a stethoscope, such as, for example, head 92 of stethoscope 94. In some embodiments, sides 78 of covers 72 are sprayed or coated with the material having adhesion and/or adherent properties. In some embodiments, the material having adhesion and/or adherent properties forms sides 78 of covers 72. That is, the material having adhesion and/or adherent properties is integrally formed with covers 72 to provide sides 78 of covers 72 with adhesion and/or adherent properties. The material having adhesion and/or adherent properties may include one or more of a cellophane, vinyl, acetate, polyethylene acrylic, butyl rubber, ethylene-vinyl acetate, natural rubber, a nitrile, silicone rubber, a styrene block copolymer, a vinyl ether and a tackifier. In some embodiments, the adhesive and/or adherent material further includes an antimicrobial and/or antiseptic material. Antiseptic materials that can be used include but are not limited to: alcohols such as ethanol, 1-propanol and 2-propanol/isopropanol or mixtures of these alcohols; sodium bicarbonate; hydrogen peroxide; benzalkonium chloride; chlorohexidine; hexachlorophene; iodine compounds; and combinations thereof. Antimicrobial materials that can be used include but are not limited to: beta-lactam antibiotics (such as penicillin, cephalosporin); protein synthesis inhibitors (such as aminoglycosides, macrolides, tetracycline, chloramphenicol, polypeptides); sulphonamides; cotrimoxazole; quinolones; anti-viral agents; anti-fungal agents; anti-cancer drugs; anti-malarial drugs; anti-tuberculosis drugs; anti-leprotic drugs; anti-protozoal drugs; and combinations thereof. In some embodiments, the antimicrobial material is at least partially removable so that at least a portion of the antimicrobial material is left behind as covers 72 are removed from a medical device or instrument, such as, for example, a stethoscope. In some embodiments, the material having adhesion and/or adherent properties is sprayed or coated with weak adhesive non-toxic glue, such as, for example, spirit gum, when additional adherency is desired. That is, the amount of adherency may be adjusted by coating or spraying the material having adhesion and/or adherent properties with the weak adhesive. In embodiments in which the material having adhesion and/or adherent properties is coated or sprayed onto 78 sides of covers 72, it is envisioned that the material having adhesion and/or adherent properties may be sprayed or coated with one or more layers of the weak adhesive before or after the material having adhesion and/or adherent properties is applied to sides 78 of covers 72, the one or more layers of the weak adhesive may be sprayed onto the material before the material is formed into sides 78 of covers 72. In some embodiments, sides 78 of covers 72 each comprise a material that accumulates static electricity to impart sides 78 of covers 72 with adhesion and/or adherent properties.

In some embodiments, covers 72 are spaced apart from one another along strip 70. That is, covers 72 do not contact one another. In some embodiments, covers 72 define an elongated band or segment, wherein one cover 72 is connected to another cover 72 by a zone of weakness, such as, for example, a series of perforations. In some embodiments, the perforations extend through the sides 78, 80 of each cover 72. In some embodiments, the perforations have a substantially rectangular or square configuration and are uniformly spaced apart from one another. In some embodiments, the perforations include a single perforation that extends the entire distance between opposite side surfaces of each of covers 72. In some embodiments, the perforations may be variously configured and dimensioned, such as, for example, oval, oblong, triangular, square, polygonal, irregular, uniform, non-uniform, offset, staggered, undulating, arcuate, variable and/or tapered, depending on the requirements of a particular application.

In some embodiments, instrument covers 72 are each sized so that they each cover the head of a standard stethoscope, such as, for example, head 92 of stethoscope 94. In some embodiments, covers 72 are each sized to cover at least a portion of a diaphragm 98 of stethoscope 94, at least a portion of head 92 and at least a portion of tubing 96 to transfer sound to ear pieces of stethoscope 94. In some embodiments, covers 72 are each sized to at least a portion of head 92 and at least a portion of tubing 96, without covering any portion of diaphragm 98 of stethoscope 94. In some embodiments, covers 72 are each about 4 inches by about 6 inches, 3 inches by about 5 inches, 2.5 inches by 4 inches, as well as any size in between. It is contemplated that various sizes can be available according to the type of medicine being practiced. For example, covers 72 for a pediatric stethoscope may be smaller in size than covers 72 for a stethoscope used for adults.

Figure 5:
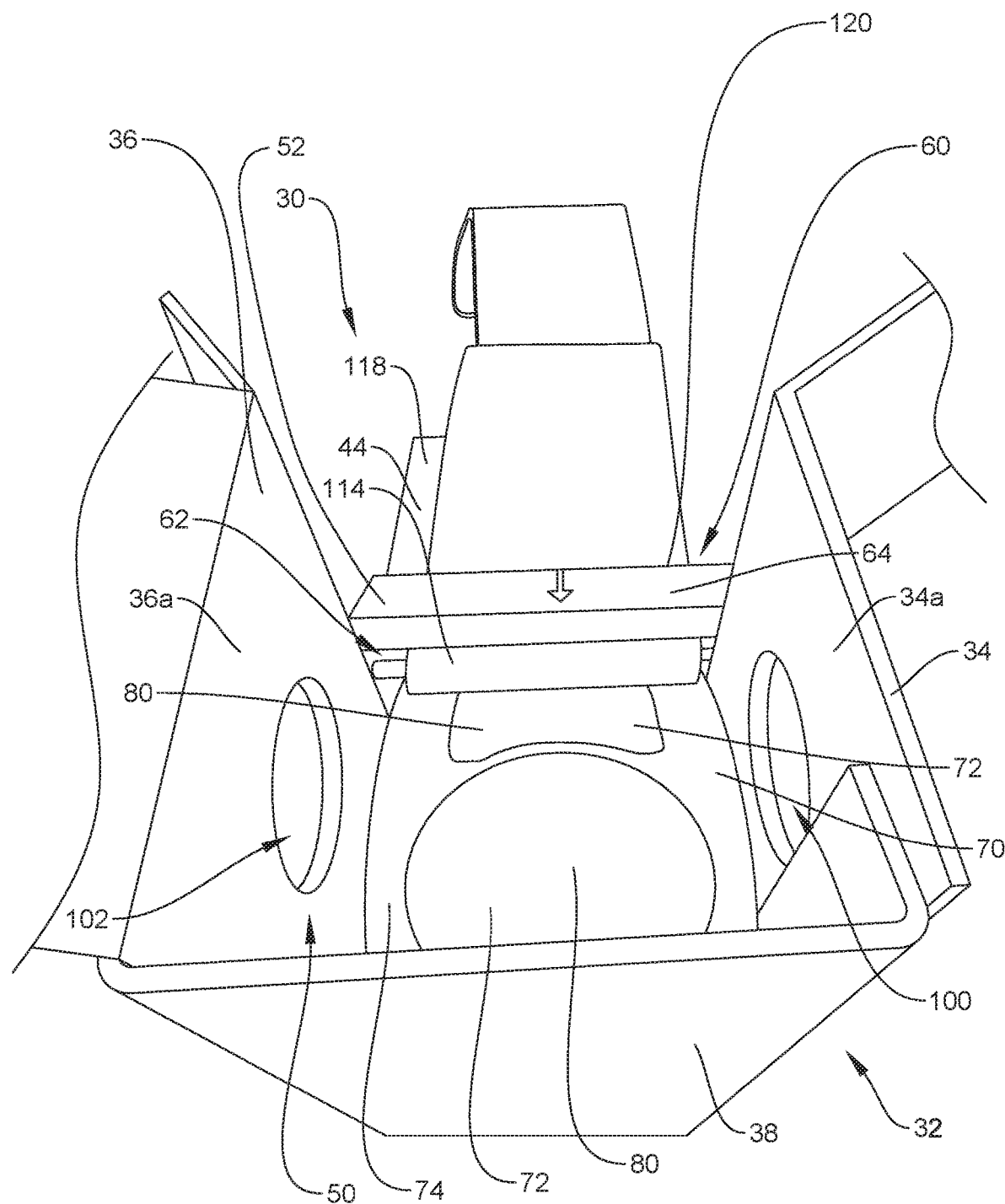
FIG. 5 is a perspective, top view of the dispensing system shown in FIG. 1, with parts separated.
Figure 6:
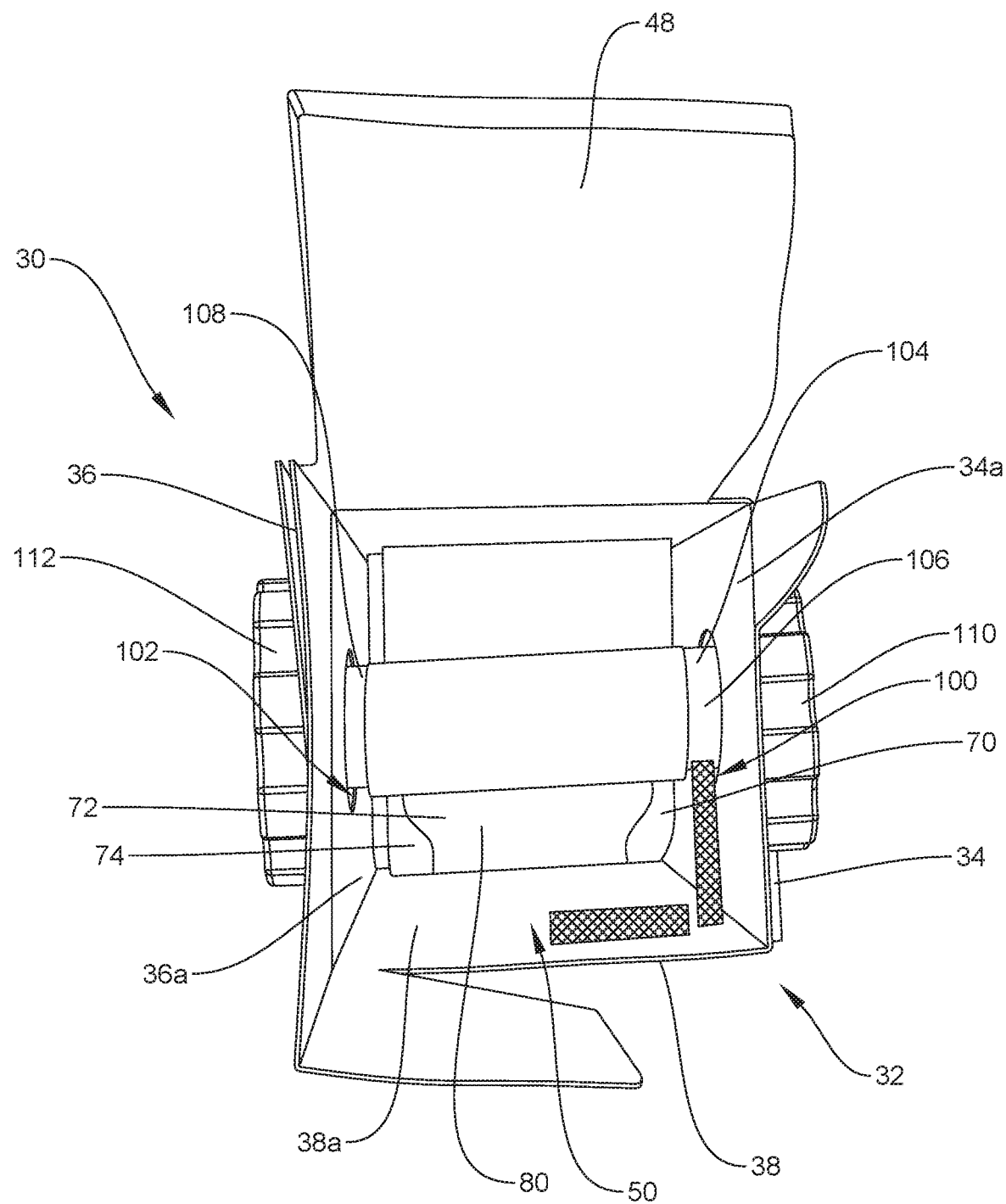
FIG. 6 is a perspective, top view of the dispensing system shown in FIG. 1, with parts separated.

Housing 32 comprises an opening 100 extending through a thickness of wall 34 and an opening 102 extending through a thickness of wall 36, as best shown in FIG. 5. Opening 102 is aligned with opening 100 such that opening 102 is coaxial with opening 100. An end 104 of a roller 106 extends through opening 100 and an opposite end 108 of roller 106 extends through opening 102, as best shown in FIG. 6. Openings 60, 62 are positioned between roll 66 and roller 106. Roller 106 is rotatable relative to housing 32 and includes a knob, such as, for example, a gripping portion 110 coupled to end 104 and a knob, such as, for example, a gripping portion 112 coupled to end 108. Gripping portions 110, 112 are positioned outside of cavity 50 and are configured to be manually gripped to rotate roller 106 relative to housing 32, as discussed herein. An intermediate portion 114 of strip 70 extends through opening 60 and over surface 64 of wedge 52. A second end 116 of strip 70 extends through opening 62 such that a portion of end 116 is wound about roller 106. In some embodiments, roll 66 defines a transverse axis X2 and roller 106 defines a transverse axis X3 that extends parallel to axis X2. In some embodiments, axes X2, X3 each extend perpendicular to axis X1. In some embodiments, roller 106 is positioned directly above roll 66 such that axis X2 is aligned with axis X3 along a vertical axis X4 that extends perpendicular to axes X1, X2, X3.

Figure 6A:
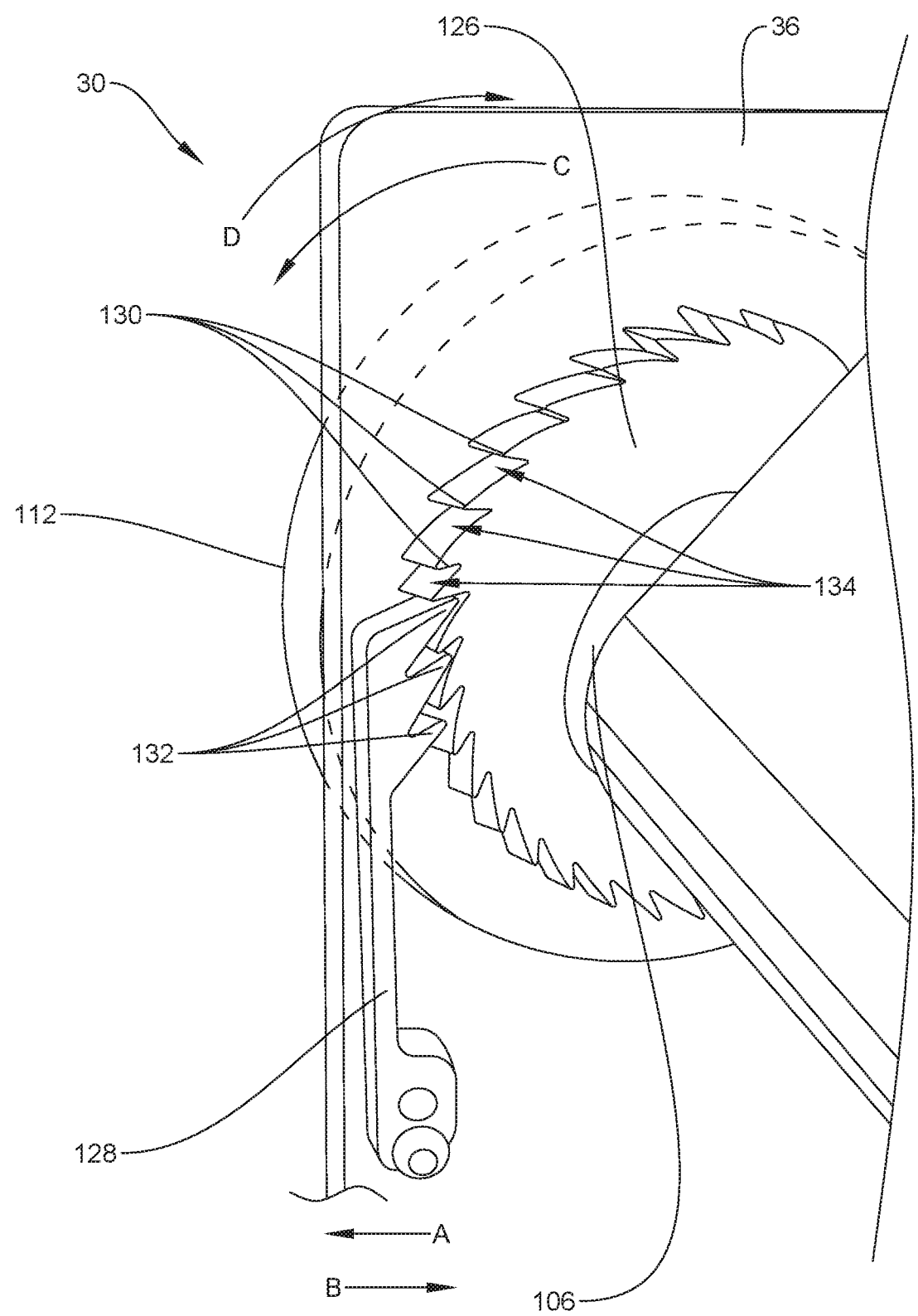
FIG. 6A is a breakaway, perspective of one embodiment of the dispensing system shown in FIG. 1 in accordance with the principles of the present disclosure.

In one embodiment, shown in FIG. 6A, housing 32 includes a ratchet portion 126 positioned between gripping portion 112 and roller 106. Housing 32 comprises a part, such as, for example, a pawl 128 that is configured to engage ratchet portion 126 to permit roller 106 to rotate relative to housing 32 about axis X3 in a first direction, such as, for example, clockwise, and prevent roller 106 from rotating relative to housing 32 about axis X3 in an opposite second direction, such as, for example, counterclockwise. In some embodiments, ratchet portion 126 comprises a plurality of teeth 130 that are configured to engage a projection 132 of pawl 128. Ratchet portion 126 comprises gaps 134 between adjacent teeth 130. In some embodiments, pawl 128 is deflectable relative to housing 32 and/or wall 36 as roller 106 is rotated about axis X3. In some embodiments, pawl 128 is deflectable relative to housing 32 and/or wall 36 in a first direction A, shown in FIG. 6A, to allow projection 132 to incrementally move from one of gaps 134 to another one of gaps 134 as roller 106 is rotated relative to housing 32 and/or wall 36 about axis X3 in one direction, such as, for example clockwise. Projection 132 is biased relative to housing 32 in an opposite second direction B to prevent roller 106 from being rotated relative to housing 32 and/or wall 36 about axis X3 in another direction, such as, for example, counterclockwise.

In some embodiments, teeth 130 are angled such that ratchet portion 126 and pawl 128 define a ratchet that allows roller 106 to be incrementally rotated relative to housing 32 and/or wall 36 about axis X3 in one direction, such as, for example, direction C, yet prevents roller 106 from being rotated relative to housing 32 and/or wall 36 about axis X3 in another direction, such as, for example, direction D. In particular, as roller 106 is rotated relative to housing 32 and/or wall 36 about axis X3 in direction C, projection 132 moves into one of gaps 134. Since pawl 128 is biased in direction B and teeth 130 are angled in the manner shown in FIG. 6A, further rotation of roller 106 relative to housing 32 and/or wall 36 about axis X3 in direction C is prevented. As roller 106 is rotated relative to housing 32 and/or wall 36 about axis X3 in direction C a first amount, projection 132 moves out of one of gaps 134 and slides along one of teeth 130. Further rotation of roller 106 relative to housing 32 and/or wall 36 about axis X3 in direction C causes projection 132 to move into one of gaps 134, since pawl 128 is biased relative to housing 32 in direction B. Roller 106 may be further rotated relative to housing 32 and/or wall 36 about axis X3 in direction C to move projection 132 such that projection 132 slides along teeth 130 to move projection 132 in and out of gaps 134 to incrementally rotate roller 103 relative to housing 32 and/or wall 36 about axis X3. This configuration allows roller 106 to be selectively rotated relative to housing 32 and/or wall 36 about axis X3 in direction C in any amount desired by a physician or medical care provider, as described herein.

In some embodiments, directions A and B and the angle of teeth 130 may be reversed such that the ratchet defined by ratchet portion 126 and pawl 128 allows roller 106 to rotate relative to housing 32 and/or wall 36 about axis X3 in direction D and prevents roller 106 from rotating relative to housing 32 and/or wall 36 about axis X3 in direction C. In some embodiments, projection 132 includes a plurality of projections 132. In embodiments where projection 132 includes a plurality of projections 132, each of projections 132 are configured for sliding along teeth 132 and disposal in one of gaps 134 in the manner discussed above. Ratchet portion 126 and pawl 128 are shown in FIG. 6A as being positioned outside of cavity 50. However, it is envisioned that ratchet portion 126 and pawl 128 can also be positioned within cavity 50. It is envisioned that housing 32 can include a ratchet portion that is the same or similar to ratchet portion 126 between gripping portion 110 and roller 106 in addition to or in place of ratchet portion 126 and housing 32 can include a pawl that is the same or similar to pawl 128 coupled to wall 34 for engagement with the ratchet portion between gripping portion 110 and roller 106. It is envisioned that the ratchet portion between gripping portion 110 and roller 106 and the pawl that engages the ratchet portion between gripping portion 110 and roller 106 can be positioned within cavity 50 or outside of cavity 50.

Figure 7:
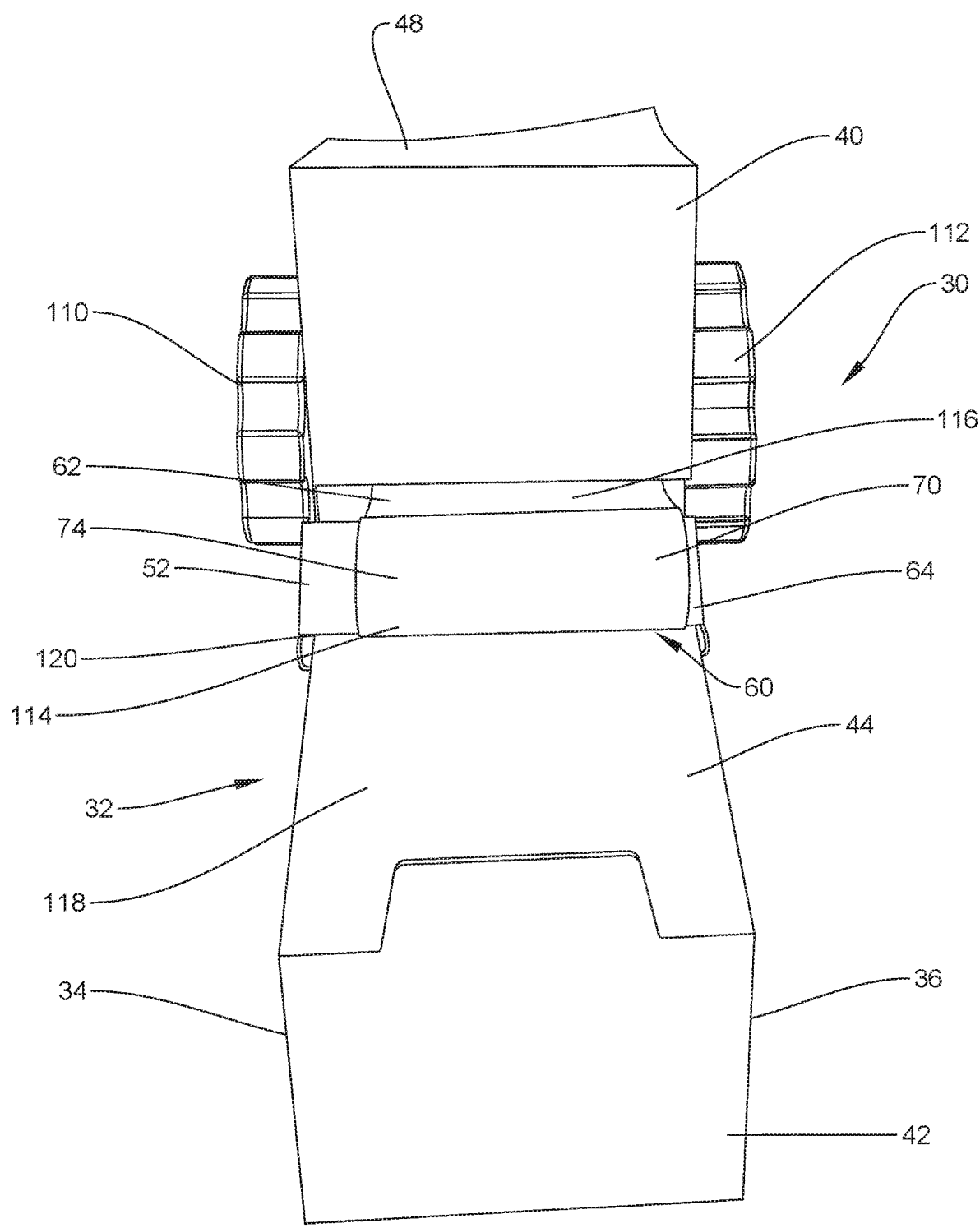
FIG. 7 is a perspective, front view of the dispensing system shown in FIG. 1.
Figure 8:
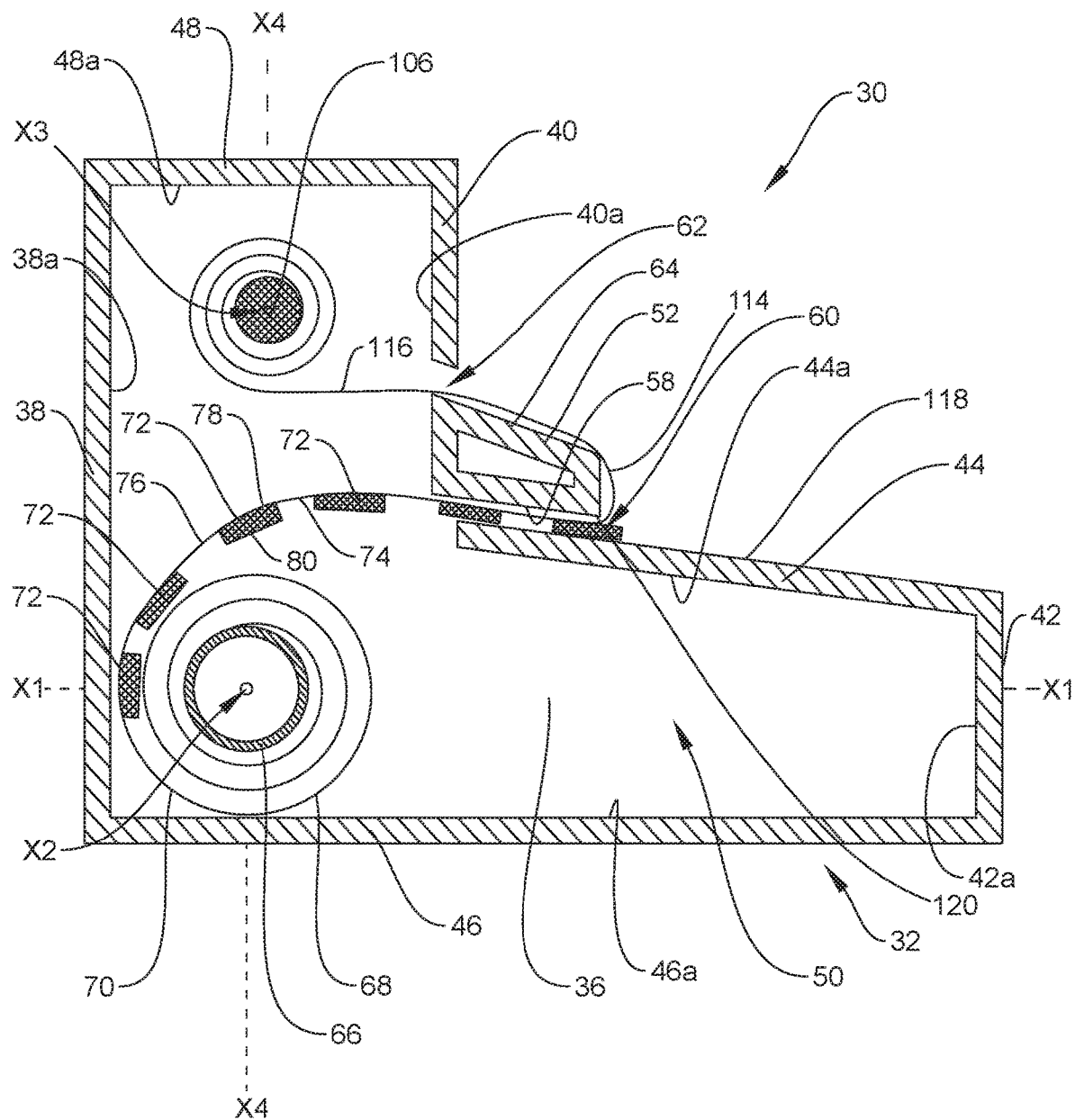
FIG. 8 is a side, cross-sectional view of the dispensing system shown in FIG. 1.
Figure 9:
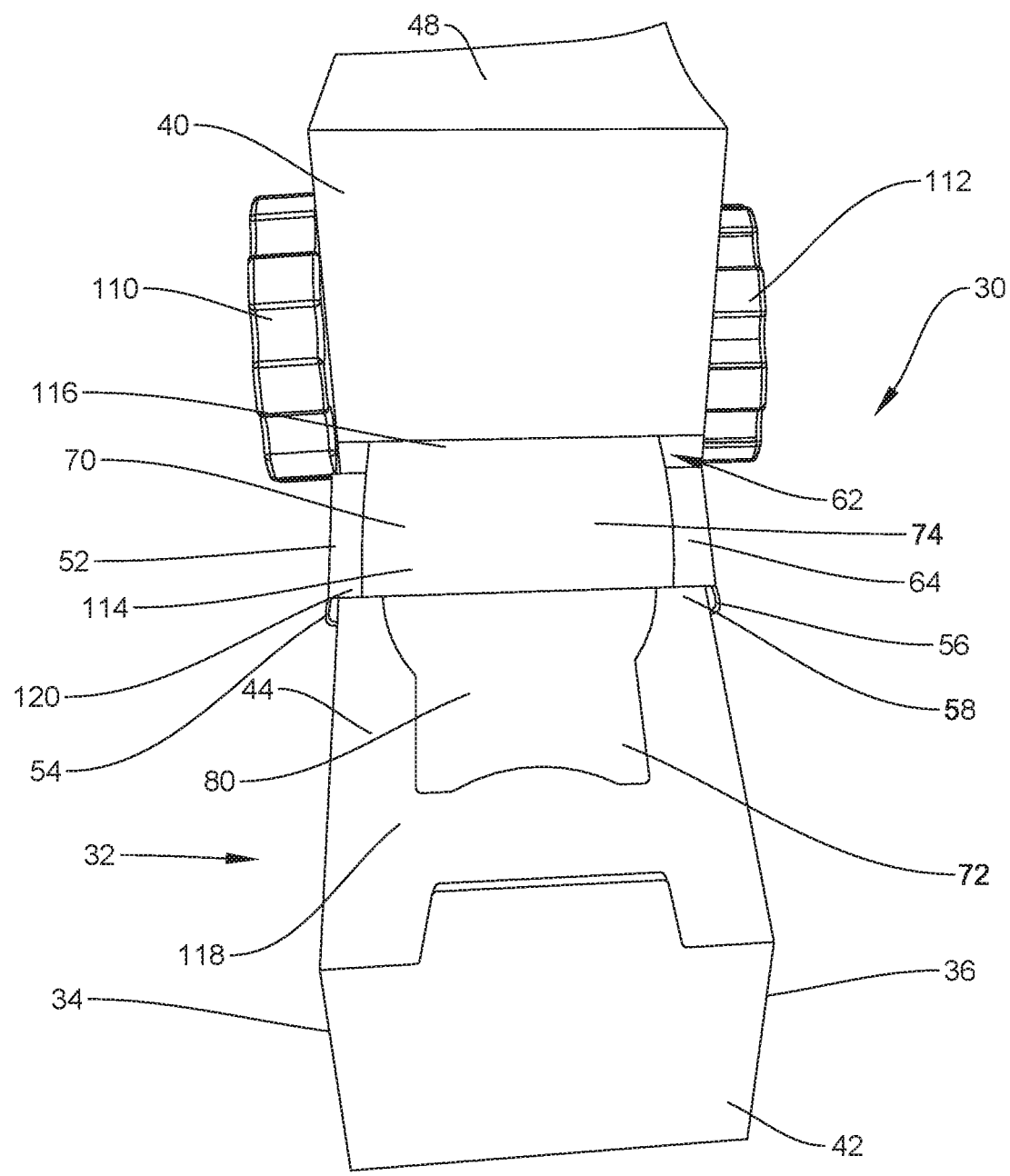
FIG. 9 is a perspective, front view of the dispensing system shown in FIG. 1.
Figure 10:
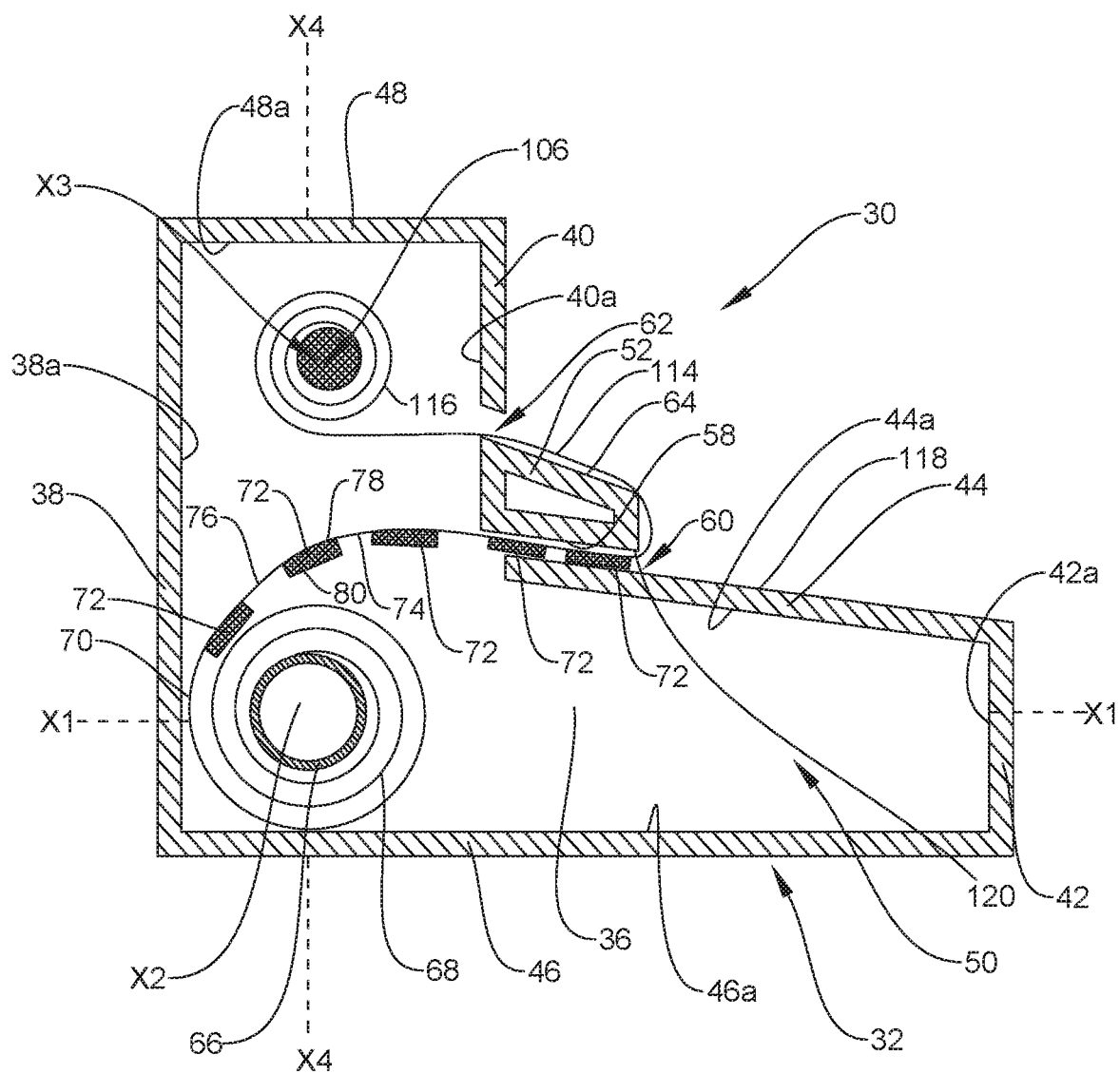
FIG. 10 is a side, cross-sectional view of the dispensing system shown in FIG. 1.
Figure 11:
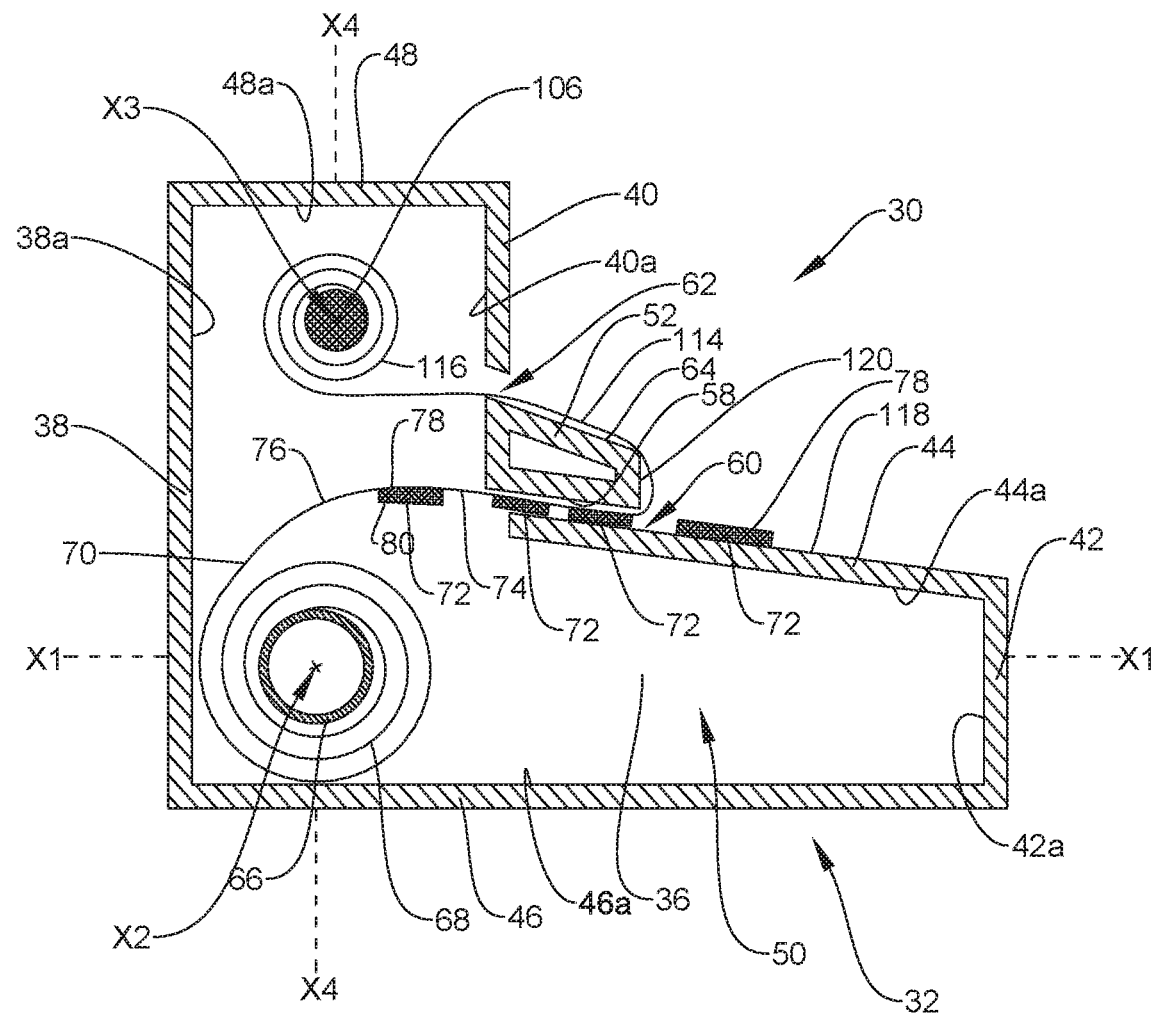
FIG. 11 is a side, cross-sectional view of the dispensing system shown in FIG. 1.

Roller 106 is rotatable relative to housing 32 to move covers 72 from a first orientation in which side 80 of a respective one of covers 72 faces and is spaced apart from an outer surface 118 of wall 44, as shown in FIGS. 7 and 8, to a second orientation in which side 80 of the respective one of covers 72 is spaced apart from strip 70 and directly engages surface 118 of wall 44, as shown in FIGS. 1 and 11. That is, side 78 directly engages strip 70 when covers 72 are in the first orientation and side 78 is spaced apart from strip 70 when covers 72 are in the second orientation. When covers 72 are in the second orientation, sides 78 face away from surface 118 for engagement with a portion of a stethoscope, as discussed herein. In some embodiments, strip 70 translates over a tip 120 of wedge 52 to move covers 72 from the first orientation to the second orientation. That is, as a portion of strip 70 extends through opening 60, side 74 of strip 70 directly engages tip 120 and surface 64 of wedge 52. As the portion of strip 70 moves into opening 62, one of covers 72 is released from strip 70 such that side 80 of one of covers 72 directly engages surface 118 of wall 44 rather than moving into opening 62. In some embodiments, tip 120 applies a force to strip 70 that is greater than the amount of force that adheres or couples covers 72 to strip 70 such that covers 72 are released from strip 70 as strip 70 translates over tip 120 of wedge 52.

Figure 6B:
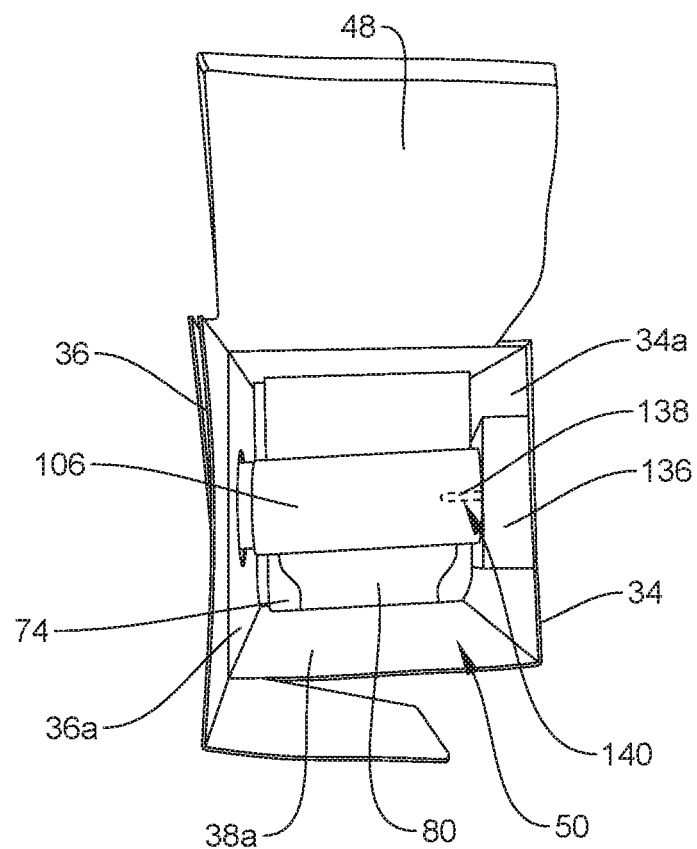
FIG. 6B is a perspective, top view, in part phantom, of one embodiment of the dispensing system shown in FIG. 1 in accordance with the principles of the present disclosure.
Figure 6C:
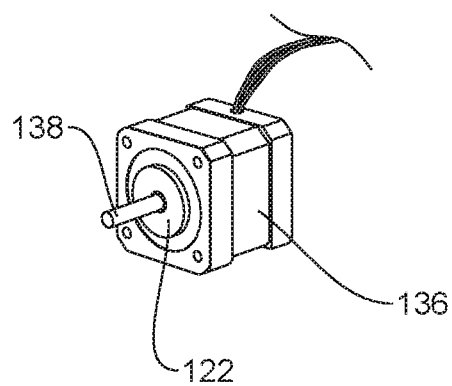
FIG. 6C is a perspective view of a component of the dispensing system shown in FIG. 6B.

In the embodiments discussed above, roller 106 is rotated manually relative to housing 32 to move covers 72 from the first orientation to the second orientation. However, it is envisioned that system 30 can include a motor or actuator 122 that is coupled to roller 106 such that actuator 122 is operable to rotate roller 106 relative to housing 32. One embodiment of actuator 122 is shown in FIG. 6. In another embodiment, shown in FIGS. 6B and 6C, actuator 122 is a stepper motor that is positioned within a housing 136. Housing 136 is configured to be positioned within cavity 50 and fixed or otherwise mounted to surface 34a or surface 36a such that an output shaft 138 that extends from actuator 122 is positioned within an aperture 140 of roller 106 such that actuator 122 rotates shaft 138 relative to housing 136 and shaft 138 rotates roller 106 relative to housing 32. In some embodiments, shaft 138 and/or aperture 140 have a non-circular cross-sectional configuration such that rotation of shaft 138 relative to housing 136 also rotates roller 106 relative to housing 32. In some embodiments, system 30 includes an on/off switch. When the on/off switch is in the off position, actuator 122 does not rotate roller 106 relative to housing 32. When the on/off switch is in the on position, actuator 122 rotates roller 106 relative to housing 32 to move covers 72 from the first orientation to the second orientation. In some embodiments, system 30 includes a sensor 124 (FIG. 2) that is in communication with actuator 122 and configured to send a signal to actuator 122 to cause actuator 122 to rotate roller 106 relative to housing 32. In some embodiments, sensor 124 sends the signal to actuator 122 based on motion detected by sensor 124. For example, in some embodiments, sensor 124 sends the signal to actuator 122 when sensor 124 detects a person approaching housing 32. In some embodiments, sensor 124 sends the signal to actuator 122 based on sound detected by sensor 124. For example, in some embodiments, sensor 124 sends the signal to actuator 122 when sensor 124 detects a person's voice and/or a specific voice command. It is envisioned that actuator 122 and/or sensor 124 can be positioned inside or outside of cavity 50.

In assembly, operation and use, a physician or medical provider can rotate roller 106 relative to housing 32 to move a first one of covers 72 from the first orientation in which side 80 of a first one of covers 72 faces and is spaced apart from outer surface 118 of wall 44, as shown in FIGS. 7 and 8, to the second orientation in which side 80 of the first one of covers 72 is spaced apart from strip 70 and directly engages surface 118 of wall 44, as shown in FIGS. 1 and 11. That is, as the first one of covers 72 moves from the first orientation to the second orientation, the first one of covers 72 is released from strip 70 such that side 80 of the first one of covers 72 is spaced apart from strip 70 and directly engages surface 118 of wall 44.

A physician or medical provider can apply the first one of covers 72 to a stethoscope, such as, for example, stethoscope 94. In some embodiments, the first one of covers 72 is applied to stethoscope 94 by positioning head 92 of stethoscope 94 such that head 92 directly engages side 78 of the first one of covers 72. Accordingly, any adhesive that was in contact with side 78 to couple covers 72 to strip will be effective to couple the first one of covers 72 to head 92. In some embodiments, a downward force is applied to head 92 to press head 92 against the first one of covers 72 such that the first one of covers 72 is positioned between head 92 and surface 118 of wall 44. Head 92 may then be moved away from housing 32 such that the first one of covers 72 moves with head 92. That is, the first one of covers 72 will adhere to head 92 such that moving head 92 away from housing 32 removes the first one of covers 72 from surface 118 of wall 44. In some embodiments, engaging head 92 with the first one of covers 72 allows the first one of covers 72 to adhere to head 92 to form a substantially air-tight seal with head 92. In some embodiments, the first one of covers 72 is crimped about head 92. In some embodiments, end 84 of the first one of covers 72 is folded or otherwise coupled to head 92 to cover at least a portion of head 92. In some embodiments, end 86 of the first one of covers 72 is folded about tubing 96 of stethoscope 94 such that end 86 adheres to tubing 96. In some embodiments, end 86 of the first one of covers 72 is crimped and/or folded about tubing 96. The physician or medical provider may then examine a first patient using stethoscope 94.

Prior to examining a second patient, the physician or medical provider may remove the first one of covers 72 from stethoscope 94 to prevent any cross-contamination from the first patient from contaminating the second patient. The first one of covers 72 may be discarded. Once the first one of covers 72 is removed from stethoscope 94, the physician or medical provider can rotate roller 106 relative to housing 32 to move a second one of covers 72 from the first orientation in which side 80 of a second one of covers 72 faces and is spaced apart from outer surface 118 of wall 44, as shown in FIGS. 7 and 8, to the second orientation in which side 80 of the first second of covers 72 is spaced apart from strip 70 and directly engages surface 118 of wall 44, as shown in FIGS. 1 and 11. That is, as the second one of covers 72 moves from the first orientation to the second orientation, the second one of covers 72 is released from strip 70 such that side 80 of the second one of covers 72 is spaced apart from strip 70 and directly engages surface 118 of wall 44. The physician or medical provider can apply the second one of covers 72 to a stethoscope, such as, for example, stethoscope 94, as discussed herein. The physician or medical provider may then examine a second patient using stethoscope 94. The second one of covers 72 may be discarded after the physician or medical provider examines the second patient. The steps discussed above may be repeated for each patient the physician or medical provider examines to prevent cross-contamination between patients.

In some embodiments, housing 32 is constructed of a single piece of material. In some embodiments, housing 32 is constructed of a single piece of material, such as, for example, cardboard. The single piece of material includes folds that allow the single piece of material to be folded to form housing 32. In some embodiments, the single piece of material is a flat piece of material. In some embodiments, the single piece of material includes tabs that allow housing 32 to remain in the folded configuration. In some embodiments, the tabs are positioned in apertures in housing 32 to allow housing 32 to remain in the folded configuration.

In the embodiments discussed above, housing 32 is configured to be directly mounted or placed on top of a surface, such as, for example, a table or directly mounted on a wall of a room, such as, for example, a doctor's office or operating room. However, it is envisioned that housing 32 can be coupled to a holder or container, such as, for example, a case 142, as shown in FIGS. 16-22. This allows case 142 to be permanently mounted to a surface such that housing 32 can be removed from case 142 after housing 32 has dispensed all of covers 72 within housing 32 and replaced with a second housing 32 that includes one or more covers 72 therein. It is envisioned that case 142 can include a means to rotate roller 106 about axis X3 to dispense covers 72 from housing 32 in the manner discussed herein. As such, roller 106 is disposed entirely within cavity 50 and does not extend through wall 34 or wall 36, as discussed herein. In some embodiments, wall 34 is free of any openings, such as, for example, opening 100 and wall 36 is free of any openings, such as, for example, opening 102.

Case 102 includes a top wall 144 and a bottom wall 146 opposite wall 144. A side wall 148 and a side wall 150 opposite wall 148 each extend from wall 144 to wall 146. Case 102 includes a back wall 152 extending from wall 144 to wall 146 and from wall 148 to wall 150. Inner surfaces of walls 144, 146, 148, 150, 152 define a cavity 154 configured for disposal of housing 32. A space between front edges of walls 144, 146 and between front edges of 148, 150 define an opening 156 that is in communication with cavity 154 such that a portion of housing 32 extends through opening 156 when housing 32 is positioned in cavity 154. For example, in some embodiments, cavity 154 has a depth such that wall 42, wall 44 and wedge 52 extend through opening 156 and are positioned outside of cavity 154 to allow a user to contact a cover 72 on wall 44 that has been dispensed from housing 32, as discussed herein.

Figure 19:
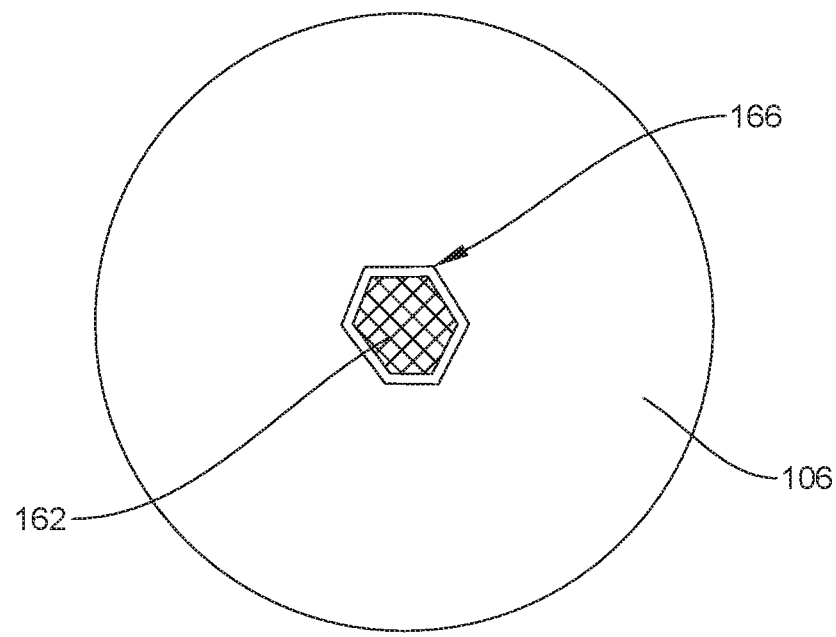
FIG. 19 is a side, cross-sectional view of components of the dispensing system shown in FIG. 16.

In some embodiments, case 142 includes a motor or actuator, such as, for example, an actuator 158 that is configured to be coupled to roller 106 to rotate roller 106 relative to housing 32 about axis X3. In some embodiments, actuator 158 is a motor, such as, for example, a stepper motor that is positioned within a housing 160 that is positioned permanently fixed to wall 148 or wall 150. An output shaft 162 extends from actuator 158. Shaft 162 extends through an opening 164 in wall 34 and is coupled to roller 106. In particular, shaft 162 extends through opening 164 and into aperture 140 of roller 106. Actuator 158 is configured to rotate shaft 162 relative to housing 160 to rotate roller 106 relative to housing 32, as discussed herein. In some embodiments, shaft 162 and aperture 140 each have a non-circular cross-sectional configuration, as shown in FIG. 19, such that rotation of shaft 162 also rotates roller 106 when shaft 162 is positioned in aperture 140. In some embodiments, shaft 162 and aperture 140 may have various cross section configurations, such as, for example, oval, oblong, triangular, rectangular, square, polygonal, irregular, uniform, non-uniform, variable and/or tapered.

Figure 17:
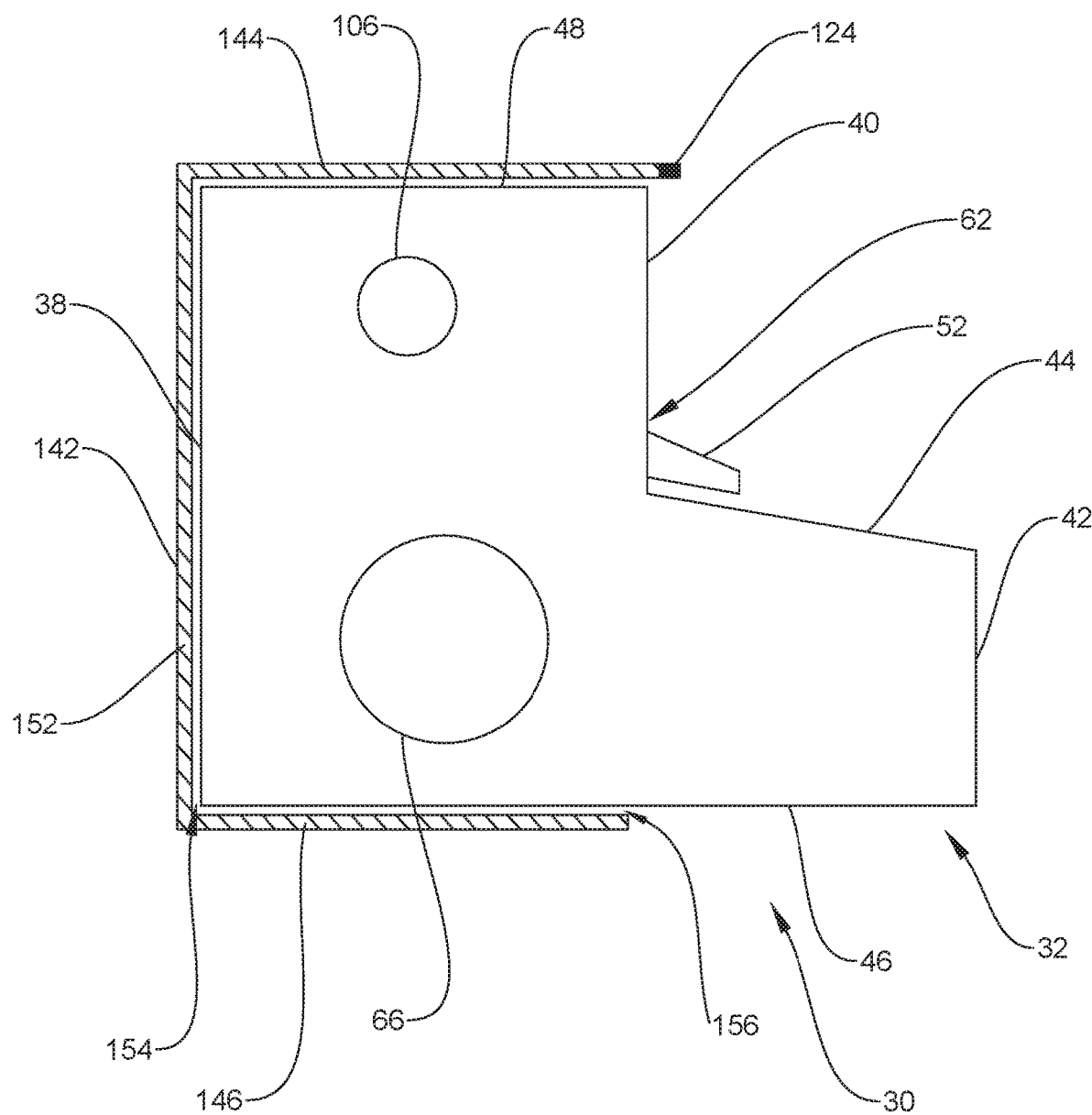
FIG. 17 is a side, cross-sectional view of components of the dispensing system shown in FIG. 16.

In some embodiments, system 30 includes an on/off switch. When the on/off switch is in the off position, actuator 158 does not rotate roller 106 relative to housing 32. When the on/off switch is in the on position, actuator 158 rotates roller 106 relative to housing 32 to move covers 72 from the first orientation to the second orientation. In some embodiments, system 30 includes a sensor, such as, for example, sensor 124 that is in communication with actuator 158 and configured to send a signal to actuator 158 to cause actuator 158 to rotate roller 106 relative to housing 32. In some embodiments, sensor 124 is coupled to case 142, as shown in FIG. 17, for example. In some embodiments, sensor 124 sends the signal to actuator 158 based on motion detected by sensor 124. For example, in some embodiments, sensor 124 sends the signal to actuator 158 when sensor 124 detects a person approaching housing 32 or case 142. In some embodiments, sensor 124 sends the signal to actuator 122 based on sound detected by sensor 124. For example, in some embodiments, sensor 124 sends the signal to actuator 158 when sensor 124 detects a person's voice and/or a specific voice command. It is envisioned that sensor 124 can be positioned inside or outside of cavity 154.

Figure 16:
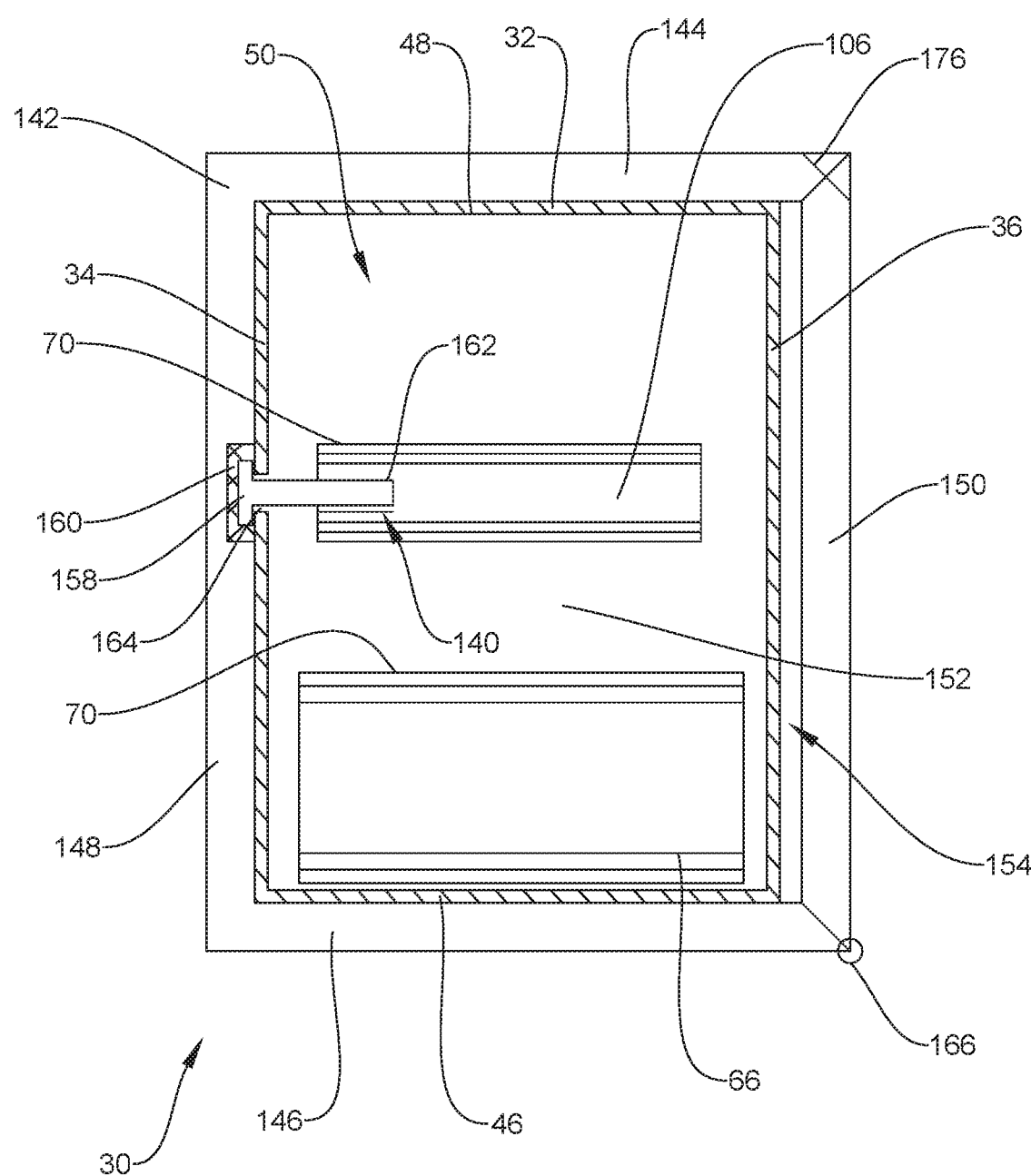
FIG. 16 is a front, cross-sectional view of one embodiment of a dispensing system in accordance with the principles of the present disclosure.
Figure 18:
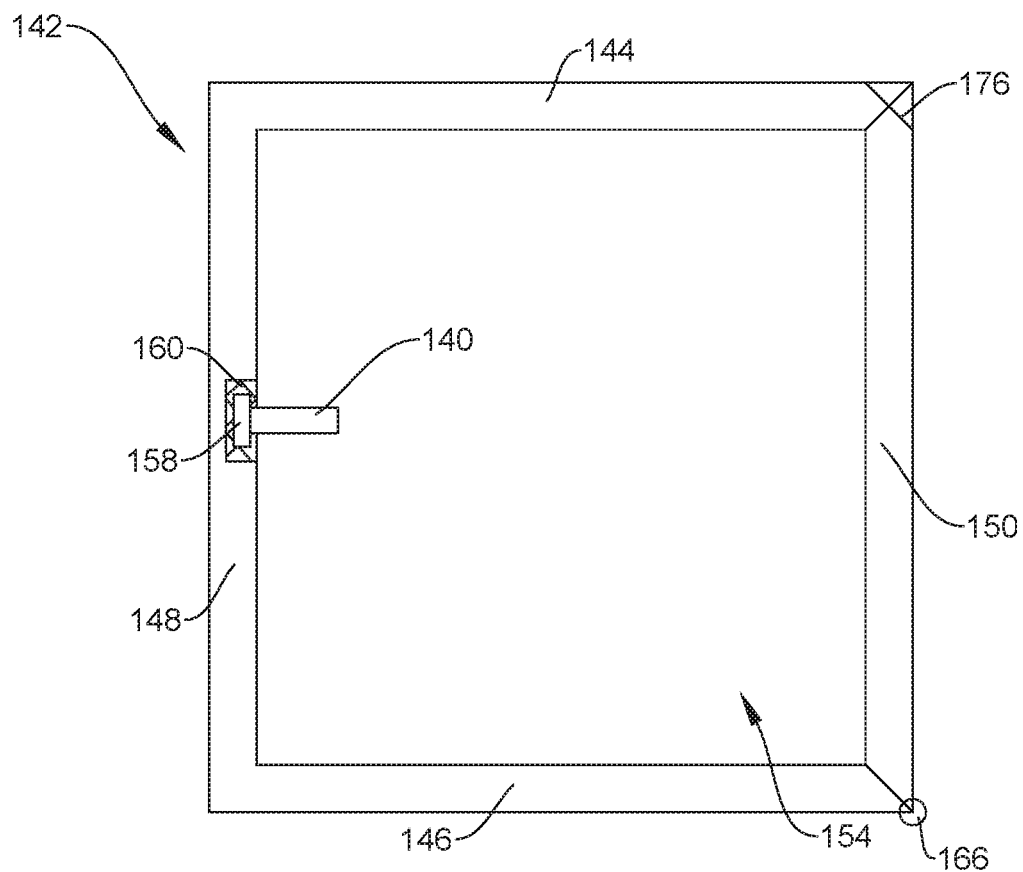
FIG. 18 is a front, cross-sectional view of a component of the dispensing system shown in FIG. 16.
Figure 20:
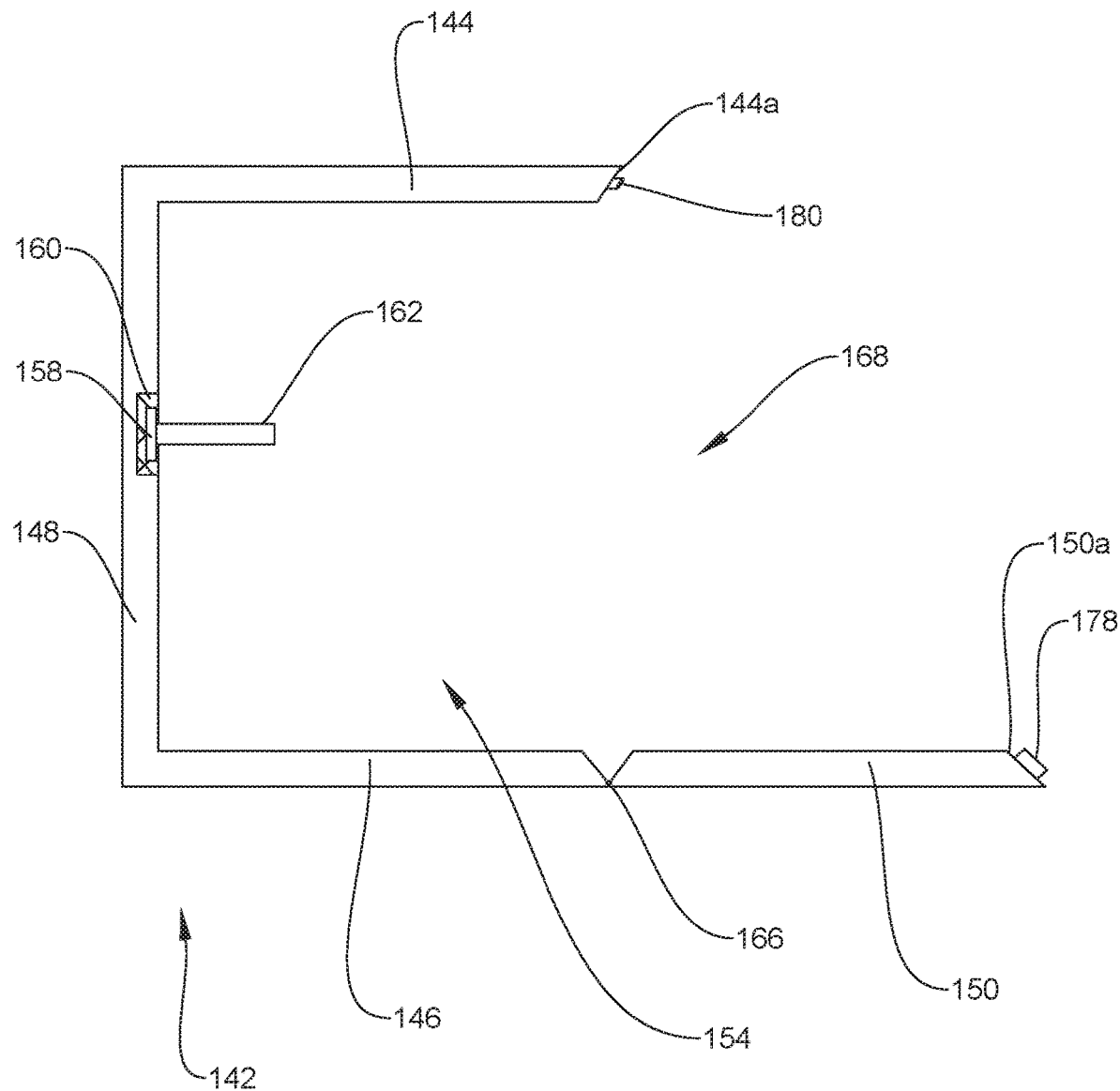
FIG. 20 is a front, cross-sectional view of a component of the dispensing system shown in FIG. 16.
Figure 21:
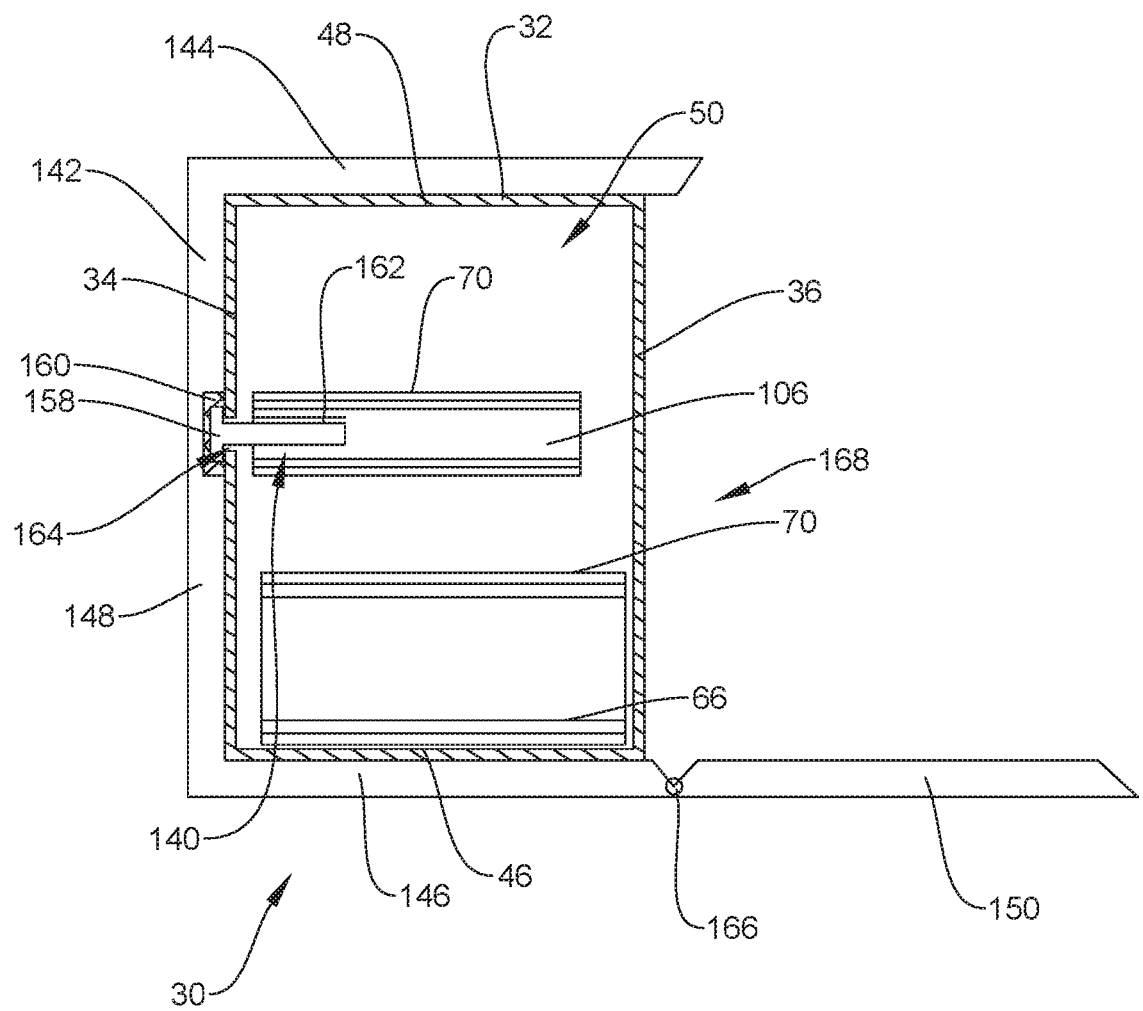
FIG. 21 is a front, cross-sectional view of components of the dispensing system shown in FIG. 16.
Figure 22:
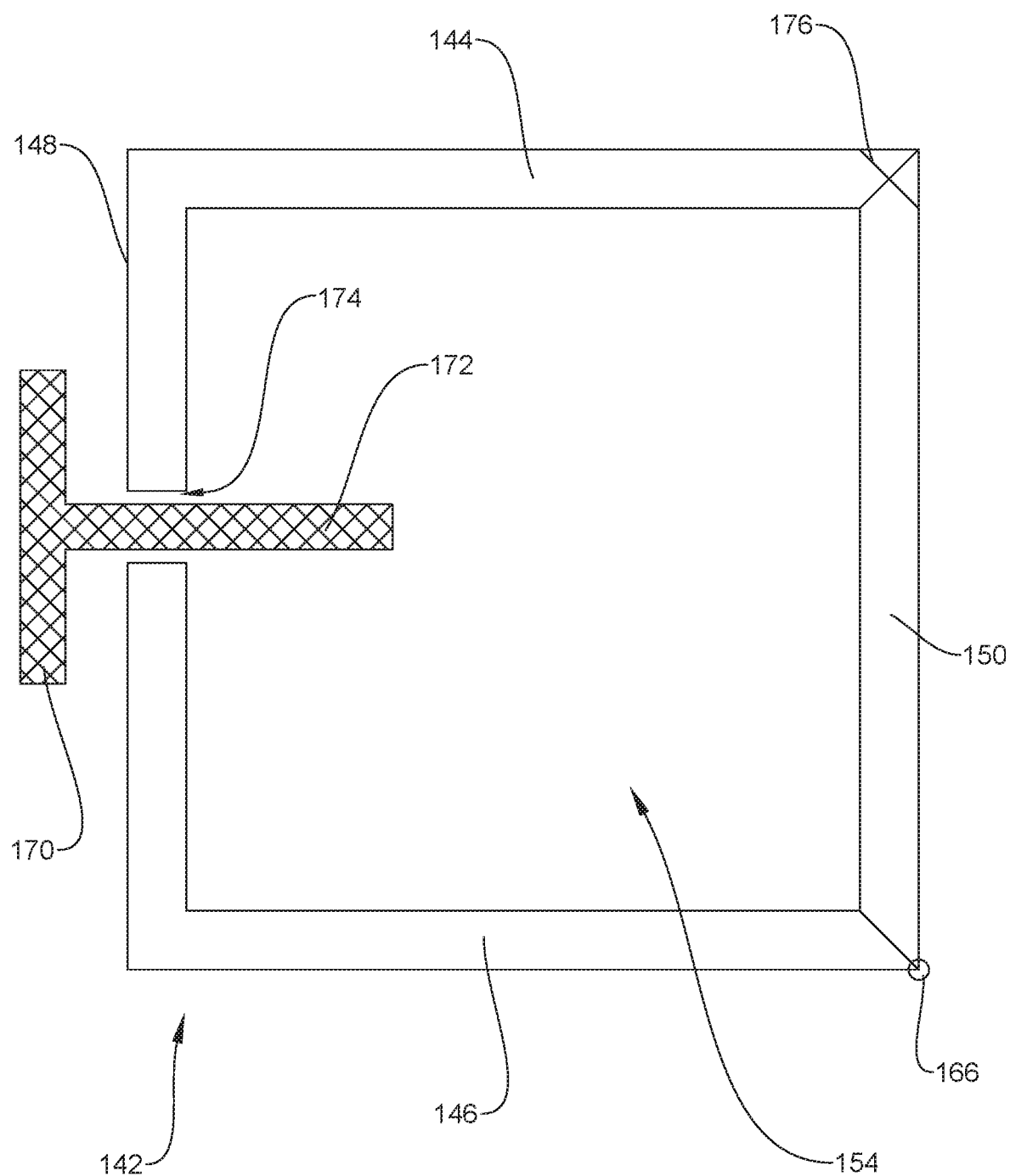
FIG. 22 is a front, cross-sectional view of one embodiment of a dispensing system in accordance with the principles of the present disclosure.

In some embodiments, case 142 is movable between an open configuration, shown in FIG. 20, and a closed configuration, shown in FIG. 18. Housing 32 is inserted into cavity 154 when case 142 is in the open configuration, as shown in FIG. 21. Case 142 is then moved from the open configuration to the closed configuration with housing 32 positioned within cavity 154 to secure housing 32 within cavity 154, as shown in FIG. 16. In some embodiments, wall 150 is pivotable relative to wall 146 about a hinge 166 to move case 142 between the open and closed configurations. When case 142 is in the closed configuration, wall 150 directly engages wall 144. When case 142 is in the open configuration, wall 150 is spaced apart from wall 144 to create an opening 168 between wall 150 and wall 144. Housing 32 is inserted through opening 168 and into cavity 154 when case 142 is in the open configuration. Case 154 is then moved from the open configuration to the closed configuration to close opening 168 and secure housing 32 within cavity 154. In some embodiments, case 142 can be provisionally retained in the closed configuration via a fastener 176 that prevents wall 150 from being uncoupled from wall 144 without applying a force greater than a force applied by fastener 176 to join wall 150 with wall 144. In some embodiments, wall 150 may be secured to wall 144 via threads, mutual grooves, screws, adhesive, nails, barbs, raised elements, spikes, clips, snaps, friction fittings, compressive fittings, expanding rivets, staples, fixation plates, key/keyslot, tongue in groove, a dovetail, a magnetic connection and/or posts to provisionally retain case 142 in the closed configuration. In one embodiment, an end 150a of wall 150 includes a magnet 178 that is configured to engage a magnet 180 on an end 144a of wall 144 to provisionally retain case 142 in the closed configuration.

In assembly, operation and use, housing 32 is inserted through opening 168 and into cavity 154 when case 142 is in the open configuration. Case 154 is then moved from the open configuration to the closed configuration to close opening 168 and secure housing 32 within cavity 154. Actuator 158 moves from an off position to an on position in response to a signal received from sensor 124 such that shaft 162 rotates roller 106 relative to housing 32 to move a first one of covers 72 from the first orientation in which side 80 of a first one of covers 72 faces and is spaced apart from outer surface 118 of wall 44, as shown in FIGS. 7 and 8, to the second orientation in which side 80 of the first one of covers 72 is spaced apart from strip 70 and directly engages surface 118 of wall 44, as shown in FIGS. 1 and 11. That is, as the first one of covers 72 moves from the first orientation to the second orientation, the first one of covers 72 is released from strip 70 such that side 80 of the first one of covers 72 is spaced apart from strip 70 and directly engages surface 118 of wall 44.

A physician or medical provider can apply the first one of covers 72 to a stethoscope, such as, for example, stethoscope 94. Prior to examining a second patient, the physician or medical provider may remove the first one of covers 72 from stethoscope 94 to prevent any cross-contamination from the first patient from contaminating the second patient. The first one of covers 72 may be discarded. Once the first one of covers 72 is removed from stethoscope 94, the physician or medical provider can provide a stimulus, such as, for example a motion or sound that causes sensor 124 to send a signal to actuator 158 such that actuator 158 causes shaft 162 to rotate roller 106 relative to housing 32 to move a second one of covers 72 from the first orientation in which side 80 of a second one of covers 72 faces and is spaced apart from outer surface 118 of wall 44, as shown in FIGS. 7 and 8, to the second orientation in which side 80 of the first second of covers 72 is spaced apart from strip 70 and directly engages surface 118 of wall 44, as shown in FIGS. 1 and 11. That is, as the second one of covers 72 moves from the first orientation to the second orientation, the second one of covers 72 is released from strip 70 such that side 80 of the second one of covers 72 is spaced apart from strip 70 and directly engages surface 118 of wall 44. The physician or medical provider can apply the second one of covers 72 to a stethoscope, such as, for example, stethoscope 94, as discussed herein. The physician or medical provider may then examine a second patient using stethoscope 94. The second one of covers 72 may be discarded after the physician or medical provider examines the second patient. The steps discussed above may be repeated for each patient the physician or medical provider examines to prevent cross-contamination between patients.

In the embodiments shown in FIGS. 16-21, case 142 is configured to rotate roller 106 automatically via actuator 158, as discussed herein. In one embodiment, shown in FIG. 22, case 142 does not include actuator 158, housing 160, or shaft 162. Rather, case 142 includes a knob 170 having a shaft 172 that extends through an opening 174 in wall 148. Shaft 172 is configured for disposal in aperture 140 of roller 106 such that rotation of knob 170 relative to wall 148 and housing 32 also rotates roller 106 relative to housing 32 to move a first one of covers 72 from the first orientation in which side 80 of a first one of covers 72 faces and is spaced apart from outer surface 118 of wall 44, as shown in FIGS. 7 and 8, to the second orientation in which side 80 of the first one of covers 72 is spaced apart from strip 70 and directly engages surface 118 of wall 44, as shown in FIGS. 1 and 11. In some embodiments, shaft 172 and aperture 140 have non-circular cross section configurations. In some embodiments, shaft 172 and aperture 140 may have various cross section configurations, such as, for example, oval, oblong, triangular, rectangular, square, polygonal, irregular, uniform, non-uniform, variable and/or tapered.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. The embodiments above can also be modified so that some features of one embodiment are used with the features of another embodiment. One skilled in the art may find variations of these embodiments, which, nevertheless, fall within the spirit of the present disclosure, whose scope is defined by the claims set forth below.

What is claimed is:

1. A dispenser comprising:
   a housing comprising opposite first and second side walls, the housing comprising a back wall and spaced apart first and second front walls, the back wall and the front walls each extending from the first side wall to the second side wall, the housing comprising an engaging wall extending from the first front wall to the second front wall, inner surfaces of the walls defining a cavity, the housing comprising a wedge extending from the engaging wall, a space between the wedge and the engaging wall defining a first opening, a space between the engaging wall and the first front wall defining a second opening, the openings being in communication with the cavity;

a roll positioned within the cavity, a first end of a strip being wound about the roll, a plurality of spaced apart covers being coupled to the strip, the covers each comprising a first side and an opposite second side, the first sides directly engaging the strip; and a roller extending through the side walls, an intermediate portion of the strip extends through the first opening and over an outer surface of the wedge, a second end of the strip extending through the second opening such that a portion of the second end is wound about the roller.

2. The dispenser recited in claim 1, wherein the roller is configured to be rotated relative to the housing manually.

3. The dispenser recited in claim 1, wherein the housing comprises a bottom wall extending from the first side wall to the second side wall and from the back wall to the second front wall, the roll being unsupported within the cavity such that a surface of the strip directly engages the bottom wall.

4. The dispenser recited in claim 1, wherein a first end of the roller extends through the first side wall and a second end of the roller extends through the second side wall, a first knob being coupled to the first end of the roller and a second knob being coupled to the second end of the roller, the knobs being positioned outside of the cavity.

5. The dispenser recited in claim 1, wherein the housing extends along a longitudinal axis between the back wall and the second front wall, the engaging surface extending at an acute angle relative to the longitudinal axis.

6. The dispenser recited in claim 1, wherein the housing extends along a longitudinal axis between the back wall and the second front wall, the roll defining a first transverse axis, the roller defining a second transverse axis, the transverse axes each extending perpendicular to the longitudinal axis, the roller being positioned directly above the roll such that the first transverse axis is aligned with the second transverse axis along a vertical axis, the vertical axis extending perpendicular to the longitudinal axis and the transverse axes.

7. The dispenser recited in claim 1, wherein the openings are positioned between the roll and the roller.

8. The dispenser recited in claim 1, wherein the housing comprises opposite top and bottom walls, the top wall extending from the first side wall to the second side wall and from the back wall to the first front wall, the bottom wall extending from the first side wall to the second side wall and from the back wall to the second front wall, the engaging wall being positioned between the top wall and the bottom wall.

9. The dispenser recited in claim 1, wherein the strip and the covers are free of any adhesive, the covers being coupled to the strip only by static electricity.

10. The dispenser recited in claim 1, wherein the strip comprises a backing paper including a first side and a second side, the first side of the backing paper being coated with a polyolefin.

11. The dispenser recited in claim 1, wherein the covers are made from a polyimide.

12. The dispenser recited in claim 1, wherein the covers are adhered to the strip by an acrylates copolymer.

13. The dispenser recited in claim 1, further comprising an actuator configured to rotate the roller relative to the housing.

14. The dispenser recited in claim 13, further comprising a sensor in communication with the actuator, the sensor being configured to send a signal to the actuator to cause the actuator to rotate the roller relative to the housing.

15. The dispenser recited in claim 1, wherein the covers are movable from a first orientation in which the second side of a respective one of the covers faces and is spaced apart from an outer surface of the engaging wall to a second orientation in which the second side of the respective one of the covers is spaced apart from the strip and directly engages the outer surface of the engaging wall.

16. The dispenser recited in claim 15, wherein the strip translates over a tip of the wedge to move the covers from the first orientation to the second orientation.

17. The dispenser recited in claim 15, wherein the covers move between the first and second orientations by rotating the roller relative to the housing.

18. The dispenser recited in claim 15, wherein the covers move from the first and second orientation as the strip translates over a tip of the wedge.

19. A dispenser comprising:

a housing comprising opposite first and second side walls, the housing comprising a back wall and spaced apart first and second front walls, the back wall and the front walls each extending from the first side wall to the second side wall, the housing comprising an engaging wall extending from the first front wall to the second front wall, inner surfaces of the walls defining a cavity, the housing comprising a wedge extending from the engaging wall, a space between the wedge and the engaging wall defining a first opening, a space between the engaging wall and the first front wall defining a second opening, the openings being in communication with the cavity;

a roll positioned within the cavity, a first end of a strip being wound about the roll, a plurality of spaced apart covers being coupled to the strip, the strip comprising a backing paper including a first side and a second side, the first side of the backing paper being coated with a polyolefin, the covers being made from a polyimide, the covers each comprising a first side and an opposite second side, an acrylates copolymer being positioned between the first sides of the covers and the polyolefin coating to couple the covers to the strip; and a roller extending through the side walls, an intermediate portion of the strip extends through the first opening and over an outer surface of the wedge, a second end of the strip extending through the second opening such that a portion of the second end is wound about the roller, wherein the roller is rotatable relative to the housing to move the covers from a first orientation in which the second side of a respective one of the covers faces and is spaced apart from an outer surface of the engaging wall to a second orientation in which the second side of the respective one of the covers is spaced apart from the strip and directly engages the outer surface of the engaging wall.

20. A dispenser comprising:

a housing comprising opposite first and second side walls, the housing comprising a back wall and spaced apart first and second front walls, the back wall and the front walls each extending from the first side wall to the second side wall, the housing comprising an engaging wall extending from the first front wall to the second front wall, inner surfaces of the walls defining a cavity, the housing comprising a wedge extending from the engaging wall, a space between the wedge and the engaging wall defining a first opening, a space between the engaging wall and the first front wall defining a second opening, the openings being in communication with the cavity;

a roll positioned within the cavity, a first end of a strip being wound about the roll, a plurality of spaced apart covers being coupled to the strip, the strip comprising a backing paper including a first side and a second side, the first side of the backing paper being coated with a polyolefin, the covers being made from a polyimide, the covers each comprising a first side and an opposite second side, an acrylates copolymer being positioned between the first sides of the covers and the polyolefin coating to couple the covers to the strip;

a roller extending through the side walls, an intermediate portion of the strip extends through the first opening and over an outer surface of the wedge, a second end of the strip extending through the second opening such that a portion of the second end is wound about the roller;

an actuator configured to rotate the roller relative to the housing; and a sensor in communication with the actuator, the sensor being configured to send a signal to the actuator in response to an audio command or a visual command detected by the sensor, the actuator being configured to rotate the roller relative to the housing upon receiving the signal from the sensor, wherein the roller is rotatable relative to the housing to move the covers from a first orientation in which the second side of a respective one of the covers faces and is spaced apart from an outer surface of the engaging wall to a second orientation in which the second side of the respective one of the covers is spaced apart from the strip and directly engages the outer surface of the engaging wall.

* * * * *